US010798955B2

(12) United States Patent
Hanna et al.

(10) Patent No.: US 10,798,955 B2
(45) Date of Patent: Oct. 13, 2020

(54) COMPOSITIONS OF PARTICULATE COFORMULATION

(71) Applicant: Nektar Therapeutics, San Francisco, CA (US)

(72) Inventors: Mazen H. Hanna, Bradford (GB); Peter York, Ilkley (GB)

(73) Assignee: Nektar Therapeutics, San Francisco, CA (US)

(*) Notice: Subject to any disclaimer, the term of this patent is extended or adjusted under 35 U.S.C. 154(b) by 0 days.

(21) Appl. No.: 15/653,059

(22) Filed: Jul. 18, 2017

(65) Prior Publication Data
US 2017/0318839 A1 Nov. 9, 2017

Related U.S. Application Data

(63) Continuation of application No. 14/841,325, filed on Aug. 31, 2015, now abandoned, which is a continuation of application No. 11/458,008, filed on Jul. 17, 2006, now Pat. No. 9,120,031, which is a continuation of application No. 10/004,522, filed on Nov. 1, 2001, now Pat. No. 7,115,280.

(30) Foreign Application Priority Data

Nov. 9, 2000 (GB) .................................. 0027353.3

(51) Int. Cl.
*A23L 5/30* (2016.01)
*A61K 9/00* (2006.01)
*A61K 9/14* (2006.01)
*A61K 9/16* (2006.01)
*A23P 10/30* (2016.01)
*B01D 9/00* (2006.01)

(52) U.S. Cl.
CPC ............. *A23L 5/30* (2016.08); *A23P 10/30* (2016.08); *A61K 9/00* (2013.01); *A61K 9/14* (2013.01); *A61K 9/167* (2013.01); *A61K 9/1694* (2013.01); *B01D 9/0054* (2013.01); *A23V 2002/00* (2013.01); *A61K 9/1652* (2013.01)

(58) Field of Classification Search
None
See application file for complete search history.

(56) References Cited

U.S. PATENT DOCUMENTS

| | | | |
|---|---|---|---|
| 4,127,235 A | 11/1978 | Klaile et al. | |
| 4,261,793 A | 4/1981 | Nakamura et al. | |
| 4,294,829 A | 10/1981 | Suzuki et al. | |
| 4,341,759 A | 7/1982 | Bogentoft et al. | |
| 4,397,907 A | 8/1983 | Rosser et al. | |
| 4,423,099 A | 12/1983 | Mueller et al. | |
| 4,476,804 A | 10/1984 | Glatt et al. | |
| 4,486,435 A | 12/1984 | Schmidt et al. | |
| 4,514,574 A | 4/1985 | Inoue et al. | |
| 4,540,602 A | 9/1985 | Motoyama et al. | |
| 4,568,559 A | 2/1986 | Nuwayser et al. | |
| 4,582,731 A | 4/1986 | Smith | |
| 4,590,206 A | 5/1986 | Forrester et al. | |
| 4,624,848 A * | 11/1986 | Lee .................... | A61K 9/2027 424/486 |
| 4,749,576 A | 6/1988 | Lee | |
| 4,760,093 A | 7/1988 | Blank et al. | |
| 4,784,878 A | 11/1988 | Haak | |
| 4,835,187 A | 5/1989 | Reuter et al. | |
| 4,898,781 A | 2/1990 | Onouchi et al. | |
| 4,919,853 A | 4/1990 | Alvarez et al. | |
| 4,923,720 A | 5/1990 | Lee et al. | |
| 4,952,402 A | 8/1990 | Sparks et al. | |
| 4,999,189 A | 3/1991 | Kogan et al. | |
| 5,000,888 A | 3/1991 | Kilbride, Jr. et al. | |
| 5,009,367 A | 4/1991 | Nielsen | |
| 5,066,522 A | 11/1991 | Cole et al. | |
| 5,178,878 A | 1/1993 | Wehling et al. | |
| 5,219,575 A | 6/1993 | Van Bommel et al. | |
| 5,221,731 A | 6/1993 | Weymans et al. | |
| 5,229,486 A | 7/1993 | Paul et al. | |
| 5,232,707 A | 8/1993 | Lokensgard | |
| 5,254,330 A | 10/1993 | Ganderton et al. | |
| 5,260,306 A | 11/1993 | Boardman et al. | |
| 5,269,980 A | 12/1993 | Levendis et al. | |
| 5,279,708 A | 1/1994 | Wood et al. | |
| 5,302,581 A | 4/1994 | Sarin et al. | |
| 5,354,562 A | 10/1994 | Platz et al. | |
| 5,354,934 A | 10/1994 | Pitt et al. | |
| 5,376,386 A | 12/1994 | Ganderton et al. | |

(Continued)

FOREIGN PATENT DOCUMENTS

DE 4041563 A1 6/1992
EP 0072046 A1 2/1983
(Continued)

OTHER PUBLICATIONS

Reverchon, E., et al, "Supercritical antisolvent precipitation of micro- and nano-particles", J. Supercritical Fluids, 1999, pp. 1-21 (Year: 1999).*

(Continued)

*Primary Examiner* — Michael G. Hartley
*Assistant Examiner* — Lance W Rider
(74) *Attorney, Agent, or Firm* — Susan T. Evans

(57) ABSTRACT

Embodiments of the invention provide a composition of a particulate coformulation which includes particles containing an active substance and an additive, wherein each particle contains a relative additive concentration increasing radially outwards from a particle center to a particle surface along a finite gradient. In one example, the particle surface is an additive-rich surface without a distinct physical boundary between the particle center and the particle surface. The relative additive concentration may have a continuous rate of change across the finite gradient. In some examples, an active substance:additive ratio of the particle surface is sufficiently low to form a protective surface layer around the active substance. Generally, the particle surface is free of the active substance.

17 Claims, 15 Drawing Sheets

(56) References Cited

U.S. PATENT DOCUMENTS

| | | |
|---|---|---|
| 5,384,133 A | 1/1995 | Boyes et al. |
| 5,424,076 A | 6/1995 | Gorissen et al. |
| 5,494,681 A | 2/1996 | Cuca et al. |
| 5,495,681 A | 3/1996 | Paradis |
| 5,510,118 A | 4/1996 | Bosch et al. |
| 5,518,187 A | 5/1996 | Bruno et al. |
| 5,518,709 A | 5/1996 | Sutton et al. |
| 5,548,004 A | 8/1996 | Mandel et al. |
| 5,554,382 A | 9/1996 | Castor |
| 5,607,697 A | 3/1997 | Alkire et al. |
| 5,622,657 A | 4/1997 | Takada et al. |
| 5,639,475 A | 6/1997 | Bettman et al. |
| 5,651,990 A | 7/1997 | Takada et al. |
| 5,667,806 A | 9/1997 | Kantor |
| 5,708,039 A | 1/1998 | Daly et al. |
| 5,709,886 A | 1/1998 | Bettman et al. |
| 5,716,558 A | 2/1998 | Nielsen et al. |
| 5,723,269 A | 3/1998 | Akagi et al. |
| 5,725,836 A | 3/1998 | Rouanet et al. |
| 5,727,333 A | 3/1998 | Folan |
| 5,776,491 A | 7/1998 | Allen, Jr. et al. |
| 5,795,594 A | 8/1998 | York et al. |
| 5,807,576 A | 9/1998 | Allen, Jr. et al. |
| 5,807,578 A | 9/1998 | Acosta-Cuello et al. |
| 5,851,453 A * | 12/1998 | Hanna ............... A61K 9/1688 264/5 |
| 5,855,913 A | 1/1999 | Hanes et al. |
| 5,874,029 A | 2/1999 | Subramaniam et al. |
| 5,916,596 A | 6/1999 | Desai et al. |
| 5,952,008 A | 9/1999 | Backstrom et al. |
| 5,976,574 A | 11/1999 | Gordon |
| 5,985,248 A | 11/1999 | Gordon et al. |
| 5,985,309 A | 11/1999 | Edwards et al. |
| 5,993,805 A | 11/1999 | Sutton et al. |
| 6,001,336 A | 12/1999 | Gordon |
| 6,017,310 A | 1/2000 | Johnson et al. |
| 6,051,257 A | 4/2000 | Kodas et al. |
| 6,057,476 A | 5/2000 | Furukawa et al. |
| 6,063,138 A | 5/2000 | Hanna et al. |
| 6,116,516 A | 9/2000 | Ganan-Calvo |
| 6,117,455 A | 9/2000 | Takada et al. |
| 6,149,941 A | 11/2000 | Schwarz et al. |
| 6,174,469 B1 | 1/2001 | Ganan-Salvo |
| 6,197,835 B1 | 3/2001 | Ganan-Salvo |
| 6,258,341 B1 | 7/2001 | Foster et al. |
| 6,290,991 B1 | 9/2001 | Roser et al. |
| 6,316,029 B1 | 11/2001 | Jain et al. |
| 6,322,897 B1 | 11/2001 | Borchert et al. |
| 6,331,290 B1 | 12/2001 | Morgan |
| 6,331,310 B1 | 12/2001 | Roser et al. |
| 6,387,410 B1 | 5/2002 | Woolfe et al. |
| 6,414,050 B1 | 7/2002 | Howdle et al. |
| 6,551,617 B1 | 4/2003 | Corbo et al. |
| 6,565,885 B1 | 5/2003 | Tarara et al. |
| 6,572,893 B2 | 6/2003 | Gordon et al. |
| 6,656,492 B2 | 12/2003 | Kajiyama et al. |
| 6,660,382 B2 | 12/2003 | Nouri et al. |
| 6,860,907 B1 | 3/2005 | Hanna et al. |
| 7,115,280 B2 | 10/2006 | Hanna et al. |
| 9,120,031 B2 | 9/2015 | Hanna et al. |
| 2002/0000681 A1 | 1/2002 | Gupta et al. |
| 2002/0071871 A1 | 6/2002 | Snyder et al. |
| 2002/0081266 A1 | 6/2002 | Woolfe et al. |
| 2002/0114844 A1 | 8/2002 | Hanna et al. |
| 2003/0047824 A1 | 3/2003 | Hanna et al. |
| 2003/0109421 A1 | 6/2003 | Palakodaty et al. |
| 2003/0124193 A1 | 7/2003 | Snyder et al. |
| 2003/0170310 A1 | 9/2003 | Wadhwa |
| 2003/0175214 A1 | 9/2003 | Staniforth et al. |
| 2003/0203036 A1 | 10/2003 | Gordon et al. |
| 2003/0215514 A1 | 11/2003 | Platz et al. |
| 2004/0071783 A1 | 4/2004 | Hanna et al. |
| 2004/0119179 A1 | 6/2004 | Perrut et al. |
| 2005/0170000 A1 | 8/2005 | Walker et al. |
| 2005/0206023 A1 | 9/2005 | Hanna et al. |
| 2015/0366241 A1 | 12/2015 | Hanna et al. |

FOREIGN PATENT DOCUMENTS

| | | |
|---|---|---|
| EP | 0122036 A1 | 10/1984 |
| EP | 0322687 A2 | 7/1989 |
| EP | 0344375 A1 | 12/1989 |
| EP | 0360340 A1 | 3/1990 |
| EP | 0383569 A2 | 8/1990 |
| EP | 0461930 A1 | 12/1991 |
| EP | 0464171 A1 | 1/1992 |
| EP | 469725 A1 | 2/1992 |
| EP | 512693 A1 | 11/1992 |
| EP | 0542314 A1 | 5/1993 |
| EP | 0611567 A1 | 8/1994 |
| EP | 628331 A1 | 12/1994 |
| EP | 0661091 A1 | 7/1995 |
| EP | 674541 A1 | 10/1995 |
| EP | 0677332 A2 | 10/1995 |
| EP | 681843 A2 | 11/1995 |
| EP | 709085 A1 | 5/1996 |
| EP | 899017 A1 | 3/1999 |
| EP | 972526 A2 | 1/2000 |
| EP | 1004349 A1 | 5/2000 |
| EP | 1022020 A2 | 7/2000 |
| EP | 1027887 A2 | 8/2000 |
| GB | 1122284 A | 8/1968 |
| GB | 2105189 A | 3/1983 |
| GB | 2322326 A | 8/1998 |
| GB | 2371501 A | 7/2002 |
| GB | 0300338.1 | 2/2003 |
| GB | 0300339.9 | 2/2003 |
| JP | 1176437 A | 7/1989 |
| JP | 7101881 A | 4/1995 |
| JP | 7101882 A | 4/1995 |
| JP | 7101883 A | 4/1995 |
| JP | 7101884 A | 4/1995 |
| JP | 4036233 B2 | 1/2008 |
| JP | 4187739 B2 | 11/2008 |
| JP | 5057166 B2 | 10/2012 |
| WO | WO 81/02975 A1 | 10/1981 |
| WO | WO 88/04556 A1 | 6/1988 |
| WO | WO 88/07870 A1 | 10/1988 |
| WO | WO 88/09163 A1 | 12/1988 |
| WO | WO 90/03782 A2 | 4/1990 |
| WO | WO 90/11139 A1 | 10/1990 |
| WO | WO 92/18164 A1 | 10/1992 |
| WO | WO 93/02712 A1 | 2/1993 |
| WO | WO 95/01221 | 1/1995 |
| WO | WO 95/01324 A1 | 1/1995 |
| WO | WO 95/21688 A1 | 8/1995 |
| WO | WO 96/00610 A1 | 1/1996 |
| WO | WO 97/14407 A1 | 4/1997 |
| WO | WO 97/31691 A1 | 9/1997 |
| WO | WO 98/13136 A1 | 4/1998 |
| WO | WO 98/17676 A1 | 4/1998 |
| WO | WO 98/29096 A1 | 7/1998 |
| WO | WO 98/36825 | 8/1998 |
| WO | WO 98/46215 A1 | 10/1998 |
| WO | WO 99/17742 A2 | 4/1999 |
| WO | WO 99/17748 A1 | 4/1999 |
| WO | WO 99/30834 A1 | 6/1999 |
| WO | WO 99/44733 A1 | 9/1999 |
| WO | WO 99/52550 A1 | 10/1999 |
| WO | WO 99/59710 A1 | 11/1999 |
| WO | WO 00/30612 A1 | 6/2000 |
| WO | WO 00/30613 A1 | 6/2000 |
| WO | WO 00/30617 A1 | 6/2000 |
| WO | WO 00/67892 A1 | 11/2000 |
| WO | WO 01/03821 A1 | 1/2001 |
| WO | WO 01/15664 A2 | 3/2001 |
| WO | WO 01/45731 A1 | 6/2001 |
| WO | WO 02/32462 A1 | 4/2002 |
| WO | WO 02/38127 A2 | 5/2002 |
| WO | WO 02/058674 A2 | 8/2002 |

(56) References Cited

FOREIGN PATENT DOCUMENTS

| WO | WO 03/008082 A1 | 1/2003 |
|---|---|---|
| WO | WO 04/098561 A2 | 11/2004 |

OTHER PUBLICATIONS

Un-I-Zahra, S., et al., "Effect of Different Parameters on the Fabrication of Sustained Release Cellulose Acetate and Ethyl Cellulose Polymer Blends", Cellulose Chemistry and Technology, pp. 901-909 (Year: 2017).*

Rials, T,G, et al., "Thermal and Dynamic Mechanical Properties of Hydroxypropyl Cellulose Films", J. Appl. Polymer Sci., pp. 749-759 (Year: 1988).*

Westmeier, R., et al., "Combination Particles Containing Salmeterol Xinafoate and Fluticasone Propionate: Formulation and Aerodynamic Assessment", J. Pharm. Sci., pp. 2299-2310 (Year: 2008).*

Al-Omran et al., "Formulation and Physicochemical Evaluations of Diciofenac Sodium Chewable Tablets", Saudi Pharmaceutical J., 10(4):177-183, (2002).

Bodmeier et al., "Polymeric Microspheres Prepared by Spraying Into Compressed Carbon Dioxide", Pharmaceutical Research, vol. 12, No. 8, pp. 1211-1217, (1995).

Chang et al., "Precipitation of Microsize Organic Particles from Supercritical Fluids", AlChE Journal, vol. 35, No. 11, pp. 1876-1882, (Nov. 1989).

Dixon et al., "Polymeric Materials Formed by Precipitation with a Compressed Fluid Antisolvent", AlChE J., vol. 39, No. O, pp. 127-139, (1993).

Ghaderi et al., "A New Method for Preparing Biodegradable Microparticles and Entrapment of Hydrocortisone in DL-PLG Microparticles Using Supercritical Fluids", European J. of Pharm. Sci., vol. 10, No. 1, pp. 1-9, (Mar. 2000).

Ghaderi, A Supercritical Fluids Extraction Process for the Production of Drug Loaded Biodegradable Microparticles (Upsaia 2000). (NEKT0003.C1).

Ghaderi et al., Preparation of Biodegradable Microparticles Using Solution-Enhanced Dispersion by Supercritical Fluids (SEDS), Pharmaceutical Research, vol. 16, No. 5, (1999). (NEKT0003.C1).

He et al., "Chitosan Microspheres Prepared by Spray Drying", International J. of Pharm. (Amsterdam), vol. 187, No. 1, pp. 53-65, (1999).

Jung et al., "Particle Design Using Supercritical Fluids: Literature and Patent Survey", J. of Supercritical Fluids, vol. 20, pp. 179-219, (2001).

Kislalioglu, "Physical Characterization and Dissolution Properties of Ibuprofen: Eudragit Coprecipates", J. Pharma. Sci., pp. 799-804, (1991).

Kovacs et al., "Hydroxyethylcellulose for Tablet Coating", Drug Dev. Ind. Pharm., 16, pp. 2302-2323, (1990).

Lehman, "Coating of Tablets and Small Particles with Acrylic Resins by Fluid Bed Technology", J. Pharm. Tech. Prod. Mfr., 2(4): pp. 3143, (1981).

Meyer et al., "Preparation and in vitro characterization of gentamycin-impregnated biodegradable beads suitable for treatment of osteomyelitis", J. of Pharm. Sci., vol. 87, No. 9, pp. 1149-1154, (Sep. 1, 1998).

Moneghini et al., "Processing of Carbamazepine-PEG 4000 Solid Dispersions with Supercritical Carbon Dioxide", International J. of Pharm., Netherlands, vol. 222, No. 1, pp. 129-138, (Jul. 3, 2001).

Phillips et al., "Rapid Expansion from Supercritical Solutions: Application to Pharmaceutical Processes", International J. of Pharmaceutics, vol. 94, pp. 1-10, (1993).

Sajeev et al., "Oral controlled release formulation of diciofenac sodium by microencapsulation with ethyl cellulose", J. Microencapsulation, 19(6):753-760, (2002).

Sanchez et al., "Development of Biodegradable Microspheres and Nanospheres for the Controlled Release of Cyclosporin", International J. of Pharmaceuticals, vol. 99, pp. 263-273, (1993).

Sandberg et al., "Inflammatogenic and adjuvant properties of HEMA in mice", Eur. J. Oral Sci., pp. 410-416, (2005).

Stafford, "Hydroxypropyl Methyphthalate as Enteric Coating for Tablets/Granules", Drug Dev. Ind. Pharm., pp. 513-530, (1982).

Tom et al., "Formation of Bioerodible Polymeric Microspheres by Rapid Expansion of Supercritical Solutions", Biotechnol. Prog., vol. 7, pp. 403-411, (1991).

Tom et al., "Particle Formation with Supercritical Fluids—A Review", J. Aerosol. Sci., 22(5):555-584, (1991).

Vudathala et al., "Microencapsulation of Solid Dispersions: Release of Griseofulvin from Griseofulving: Phospholipid Correcipitates in Microspheres", PharM. Research, vol. 9, No. 6, pp. 759-763, (1992).

Kidshealth.org. "Dehydration", 2002, source http://replay.waybackmachine.org/200211171135297/http://endoflifecare.tripod.com/juvenilehuntingondisease/id5.html.pp1-5.

European Patent Office's Notice of Opposition to a European patent dated Oct. 8, 2008. (NEKT0003.C1).

Proprietor's letter dated Feb. 9, 2005. (NEKT0003.C1).

Proprietor's letter dated Jun. 15, 2006. (NEKT0003.C1).

* cited by examiner

Map based on band at 1370 cm-1

COMPOSITIONS OF PARTICULATE COFORMULATION

CROSS-REFERENCE TO RELATED APPLICATIONS

This application is a continuation of U.S. patent application Ser. No. 14/841,325, filed Aug. 31, 2015, now abandoned, which is a continuation of U.S. patent application Ser. No. 11/458,008, filed Jul. 17, 2006, now U.S. Pat. No. 9,120,031, which is a continuation of U.S. patent application Ser. No. 10/004,522, filed Nov. 1, 2001, now U.S. Pat. No. 7,115,280, which claims priority to GB 0027353.3, filed Nov. 9, 2000, all of which are incorporated by reference herein in their entireties.

BACKGROUND OF THE INVENTION

Field of the Invention

This invention relates to methods for preparing particles of an active substance which have a layer of an additive, such as a taste masking additive, at the particle surfaces. The invention also relates to the particulate products of such methods.

Description of the Related Art

There are a number of reasons why a particulate active substance (such as a drug) might need a protective barrier at the particle surfaces. The active substance may be physically or chemically unstable, or incompatible with another substance with which it needs to be formulated. It may need protection against, for example, moisture, light, oxygen or other chemicals. A surface coating may alternatively be needed to delay release of the active substance for a desired time period or until it reaches an appropriate site, or to target its delivery to such a site. Drugs intended for oral administration may need coatings to mask their flavor and render them more palatable to patients.

To protect an active substance in this way, a protective additive needs to be coated onto the external surfaces of the active particles. Several methods are known for applying such coatings. Traditional pan or fluidized bed techniques apply a fluid coating directly to solid active particles. Alternatively, a thin film layer of a coating material may be deposited onto particle surfaces by adding the particles to a solution of the coating material and then removing the solvent, for instance by evaporation, spray drying or freeze drying. Plasticizers, such as polyethylene glycol (PEG), may be added to the solution to enhance coating flexibility and surface adhesion. This technique is widely used in the pharmaceutical industry to coat solid drug dosage forms such as tablets, granules and powders.

With changing trends in drug delivery, there is a growing need for direct coating of drug particles, especially fine particles. Traditional coating methods, as described above, involve several stages such as crystallizing, harvesting, drying, milling and sieving of the drug to obtain particles of the desired size range, and a subsequent, separate, coating step. This increases the risks of product loss and contamination.

The coating of microfine particles, for instance in the range 0.5-100 μm, has often proved particularly problematic due to the large surface area of the particles and the non-uniform, often incomplete, coatings achieved using traditional pan or fluidized bed coating techniques. Problems can be particularly acute if the particles are irregular in shape. If the material to be coated is water soluble, organic solvents are needed for the coating solution, which can lead to toxicity, flammability and/or environmental problems. The coatings achieved can often cause problems such as increased particle aggregation and increased residual solvent levels, which in turn can have detrimental effects on downstream processing.

In the particular case of taste masking coatings, the need for a continuous and uniform coating layer is particularly great, since any discontinuity in the coating, allowing release of even the smallest amount of a poor tasting active substance, is readily detectable. Thus, the above described problems with prior art coating techniques assume even greater significance in the case of taste masking.

Recent developments in the formation of particulate active substances include processes using supercritical or near-critical fluids as anti-solvents to precipitate the active substance from solution or suspension. One such technique is known as SEDS™ ("Solution Enhanced Dispersion by Supercritical fluids"), which is described in WO-95/01221 and, in various modified forms, in WO-96/00610, WO-98/36825, WO-99/44733, WO-99/59710, WO-01/03821 and WO-01/15664, which are hereby incorporated in their entirety by reference. The literature on SEDS™ refers to the possibility of coating fine particles, starting with a suspension of the particles in a solution of the coating material (see in particular WO-96/00610, page 20 line 28-page 21 line 2, also WO-95/01221 Example 5).

Distinct from the coating of particulate actives, it is also known to mix active substances such as drugs with excipients (typically polymers) which serve as carriers, fillers and/or solubility modifiers. For this purpose the active substance and excipient are ideally coformulated to yield an intimate and homogeneous mixture of the two. Known techniques include co-precipitation of both the active and the excipient from a solvent system containing both. The SEDS™ process may also be used to coformulate in this way, as described for instance in WO-95/01221 (Examples 10 and 16), WO-01/03821 (Examples 1-4) and WO-01/15664.

The products of coformulation processes are generally intimate mixtures of the species precipitated, for instance a solid dispersion of a drug within a polymer matrix. This is particularly the case for the products of a very rapid particle formation process such as SEDS™ (see the above literature). Indeed, because prior art coformulations have for the most part been motivated by the need to modify the dissolution rate of an active substance, they have concentrated (as in WO-01/15664) on obtaining truly homogeneous mixtures of the active and excipient(s), with the active preferably in its more soluble amorphous, as opposed to crystalline, state.

While such a high degree of mixing is desirable for many products, it is clearly not appropriate where the additive is a surface protector or taste masking agent, since it leaves at least some of the active substance exposed at the particle surfaces, while "tying up" a significant proportion of the additive within the particle core. In the case of an unpleasant-tasting drug, even very tiny amounts at the particle surfaces can be sufficient to stimulate the taste buds, despite the additional presence of a taste masking agent.

Where such prior art formulations failed to achieve a completely homogeneous dispersion of the active in the excipient, for instance at higher active loadings, SEM analysis suggested that they contained domains of purely crystalline, excipient-free active substance. These domains would be expected to be surrounded by a second phase containing a homogeneous mixture of the remaining active and the excipient. This too would be highly undesirable for taste-masked or otherwise surface-protected systems; at least some of the active would still be present at the particle surfaces. For this reason, active/excipient coformulation has tended to be used for systems containing lower active loadings, in order to achieve intimate homogeneous mixtures of the active (preferably in its amorphous phase) and the excipient. Alternative techniques, using physically distinct active and excipient phases, have been used to achieve coating of actives, especially at relatively high active:excipient ratios.

Thus coformulation, in particular via SEDS™ as in WO-01/15664, has not previously been used to coat active substances with protective agents such as taste maskers.

SUMMARY OF THE INVENTION

It has now surprisingly been found, however, that the SEDS™ process can be used to prepare a particulate coformulation of an active substance and an additive, generally a protective additive, in which the active substance is sufficiently protected, at the particle surfaces, for the process to be of use in preparing taste masked or otherwise surface-protected drugs. The process can generate particles in which the active substance:additive concentration ratio varies across their radius, the surface having a sufficiently high additive concentration to "protect" (which includes masking) the active substance, but the core of the particle containing a significantly higher concentration of the active. Thus, although the particles are not strictly "coated", i.e., they generally possess no distinct physical boundary between a core and a coating layer, nevertheless they can behave as though coated.

In this way, a SEDS™ process can provide an extremely advantageous method for "coating" and protecting active substances. The SEDS™ process, as discussed in WO-95/01221 and the other documents listed above, can bring with it a number of general advantages, such as environmental friendliness, versatility and an extremely high degree of control over the physicochemical properties (particle size and morphology, for example) of the product. It also allows the single-step production of multi-component products.

DETAILED DESCRIPTION

Figure 1:
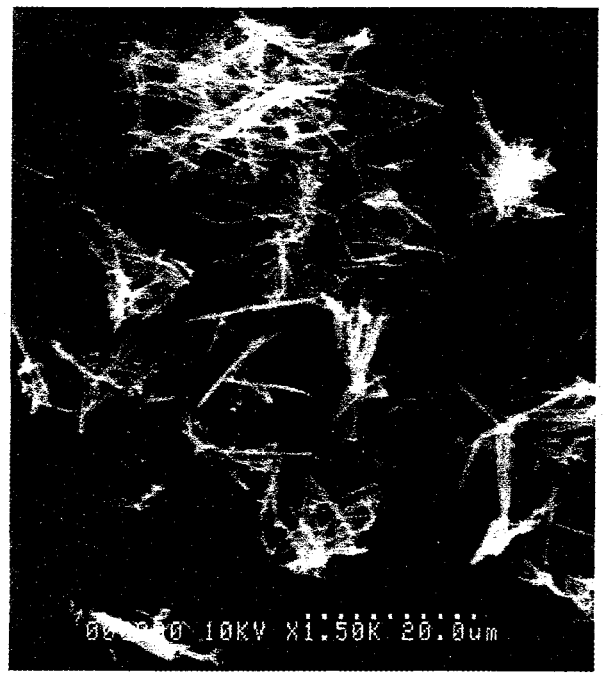
FIGS. 1-9 are scanning electron microscope (SEM) photographs of some of the products and starting materials for Examples A1 to A10 below.

According to a first aspect of the an embodiment of the invention, there is therefore provided a method for preparing particles of an active substance having a layer of an additive at the particle surfaces, the method involving dissolving both the active substance and the additive in a vehicle to form a target solution, and contacting the target solution with an anti-solvent fluid using a SEDS™ particle formation process, to cause the active substance and additive to co-precipitate.

In the following description, unless otherwise stated, references to the crystallinity, morphology, particle growth rate, solubility and miscibility of a material refer to the relevant properties under the operating conditions (for example, pressure, temperature, nature of reagents) used for the particle formation step.

By "active substance" is meant a substance capable of performing some useful function in an end product, such as a pharmaceutical product, a nutritional product, an herbicidal product, or a pesticidal product. The term is intended to embrace substances whose function is as a carrier, diluent or bulking agent for the additive (for instance, in food products, a polymer such as a cellulosic polymer may be coated with a pleasant tasting additive such as a sugar, to yield a product having the desired flavor but with a reduced additive concentration).

The active substance may be a single active substance or a mixture of two or more. It may be monomeric, oligomeric or polymeric, organic (including organometallic) or inorganic, hydrophilic, or hydrophobic. It may be a small molecule, for instance a synthetic drug like paracetamol, or a larger molecule such as a polypeptide, an enzyme, an antigen or other biological material. It is typically (although not necessarily) crystalline or semi-crystalline, preferably crystalline, by which is meant that it is capable of existing in a crystalline form under the chosen operating conditions.

The active substance preferably comprises a pharmaceutically active substance, although many other active substances, whatever their intended function (for instance, herbicides, pesticides, foodstuffs, nutraceuticals, dyes, perfumes, cosmetics, detergents, etc. ... ), may be coformulated with additives in accordance with the invention.

In particular the active substance may be a material (such as a drug) intended for consumption, which has an unpleasant taste and/or odor and needs to be coated with a taste masking agent. Examples include, but are not limited to, the bitter tasting anti-malarial drugs quinine sulphate and chloroquine; many oral corticosteroids such as are used for asthma treatment; many antibiotics; Dicyclomine HCl (anti-spasmodic); dipyridamole (platelet inhibitor); Toprimate (anti-epileptic); Oxycodone (analgesic); Carispodol (used in the treatment of hyperactivity of skeletal muscles); Bupropion (anti-depressant); Sumatripan (used in migraine treatment); Verapamil HCl (calcium ion flux inhibitor); Tinidazole (anti-parasitic); acetyl salicylic acid (aspirin, anti-pyretic); Cimetidine HCl (used in the treatment of acid/peptic disorders); Diltiazem HCl (anti-anginal); theophylline; paracetamol; and Orphenadrine citrate (anti-muscarinic). Clearly this list is not exhaustive.

The active substance may be a material which requires a protective coating because it is sensitive to heat, light, moisture, oxygen, chemical contaminants or other environmental influences, or because of its incompatibility with other materials with which it has to be stored or processed.

Active substance instability can be a particularly acute problem in the case of pharmaceuticals, since degradation can lead not only to a reduction in the active substance concentration or its bioavailability, but also in cases to the generation of toxic products and/or to an undesirable change in physical form or appearance. The most common reasons for degradation of drug substances exposed to atmospheric stresses are oxidation, hydrolysis and photochemical decomposition.

Actives susceptible to hydrolysis typically contain one or more of the following functional groups: amides (e.g., as in dibucaine, benzyl penicillin, sodium chloramphenicol and ergometrine); esters (e.g., as in procaine, tetracaine, methyladopate and physostigmine); lactams (e.g., as in cephalosporin, nitrazepam and chlorodiazeproxide); lactones (e.g., as in pilocarpine and spironolactone); oximes (e.g., as in steroid oximes); imides (e.g., as in glutethimide and ethosuximide); malonic urease (e.g., as in barbiturates); and nitrogen mustards (e.g., as in melphalan).

Actives that undergo photochemical decomposition include hydrocortisone, prednisolone, some vitamins such as ascorbic acid (vitamin C), phenothiazine and folic acid. Those that can be affected by oxidative degradation, often under ambient conditions, include morphine, dopamine, adrenaline, steroids, antibiotics and vitamins.

In some cases, however, it may be preferred for the active substance not to be ascorbic acid.

The additive may also be a single substance or a mixture of two or more, and may be monomeric, oligomeric or polymeric (typically either oligomeric or polymeric). It may be organic (including organometallic) or inorganic, hydrophilic or hydrophobic. It is typically a substance capable of protecting an active substance from external effects such as heat, light, moisture, oxygen or chemical contaminants, and/or of reducing incompatibilities between the active substance and another material with which it needs to be processed or stored, and/or of delaying, slowing or targeting the release of the active substance (for instance, for drug delivery systems), and/or of masking the flavor and/or odor of an active substance, when applied to the surface of the active substance. It is preferably non-toxic and pharmaceutically acceptable. In particular it may be a hydrophobic polymer such as an ethyl cellulose.

The additive may in particular be a taste and/or odor masking agent, in which case it should be a flavor and odor-free, or at least a pleasant tasting and smelling material, preferably hydrophobic, which is not significantly degraded by saliva during the typical residence times of a consumable product, such as a drug or foodstuff, in a consumer's mouth. Water insoluble polymers are particularly suitable as taste masking agents.

Instead or in addition, the function of the additive may be to delay release of the active substance and/or to target its delivery to a predetermined site or reagent species. This is of particular use when the active substance is a pharmaceutical (for example, drug delivery can be targeted to the intestines and colon using a coating which is insoluble in gastric fluids), but may also be necessary for instance to delay the onset of a chemical reaction involving the active substance.

In some cases, the additive may itself be an "active" (e.g., pharmaceutically active) substance, for instance where two or more drugs are to be co-administered but one must be released before another.

Examples of pharmaceutically acceptable additives include celluloses and cellulose derivatives (e.g., ethyl cellulose (hydrophobic coating agent), hydroxyethyl cellulose (commonly used for tablet coatings), hydroxypropyl cellulose and hydroxypropyl methyl cellulose); polymers incorporating phthalate groups, such as hydroxypropyl methyl phthalate (used as an enteric coating for tablets and granules); acrylates and methacrylates, such as the polymethyl acrylates and methacrylates available as Eudragit™; polyoxyalkylenes, such as polyoxyethylene, polyoxypropylene and their copolymers which are available for instance as Poloxamer™, Pluronic™ and Lutrol™; vinyl polymers such as polyvinyl alcohol; homo- and co-polymers of hydroxy acids such as lactic and glycolic acids; and mixtures thereof. These are all amorphous or, in the case of (co)polymers incorporating lactic acid, semi-crystalline.

Other commonly used coating additives include naturally occurring gums such as shellac, and many lipidic materials, examples being lecithin, waxes such as carnauba wax and microcrystalline wax, and phospholipids such as DPPC (dipalmitoyl phosphatidyl choline). The additive may be or contain flavorings, including sugars and sweeteners. Again, these lists are by no means exhaustive.

Preferred additives are those which are amorphous or semi-crystalline, most preferably amorphous, in nature. Suitably the additive is oligomeric or polymeric; most preferably it is a polymeric material. It also preferably has film forming capabilities, under the operating conditions used; polymers known to have such capabilities include ethyl cellulose, hydroxypropyl cellulose and hydroxypropyl methyl cellulose.

It may in cases, in particular where the active substance is crystalline or semi-crystalline, be unsuitable for the additive to be polyvinyl pyrrolidone (PVP), since this is known to inhibit crystallization and may lead to a homogeneous, amorphous active/additive dispersion rather than a "coated"-type system.

In some cases it may be preferred for the additive not to be a cationic polymer or copolymer, in particular not a cationic copolymer synthesized from acrylates and/or methacrylates such as from dimethylaminoethyl methacrylate and neutral methacrylic acid esters.

In certain cases it may be preferred for the additive not to be a homo- or co-polymer of hydroxy acids such as lactic and glycolic acids, in particular not to be poly(glycolic acid).

It may also be unsuitable, if the active substance is paracetamol, theophylline or ascorbic acid, in particular ascorbic acid, for the additive to be a hydrophobic polymer, in particular ethyl cellulose. If the active substance is ketoprofen, it may be unsuitable for the additive to be hydroxypropyl methyl cellulose.

The active substance and/or the additive may be formed from an in situ reaction (i.e., a reaction carried out immediately prior to, or on, contact with the anti-solvent fluid) between two or more reactant substances each carried by an appropriate vehicle.

The vehicle is a fluid capable of dissolving both the active substance and the additive, the solubility of the active substance and the additive in the vehicle being preferably 0.5-40% w/v, more preferably 1-20% w/v or 1-10% w/v. In particular, the vehicle should form, with the active and the additive, a single-phase solution rather than for instance an emulsion or other form of colloidal dispersion.

The concentration of the additive in the target solution is suitably (particularly in the case of a polymeric additive) 10% w/v or less, more suitably 5% w/v or less, such as between 1 and 2% w/v.

The vehicle must be miscible with the anti-solvent fluid under the operating conditions used to carry out the SEDS™ process. (By "miscible" is meant that the two fluids are miscible in all proportions, and/or that they can mix sufficiently well, under the operating conditions used, as to achieve the same or a similar effect, i.e., dissolution of the fluids in one another and precipitation of the active substance and additive.) The vehicle and anti-solvent are preferably totally miscible in all proportions, again under the operating conditions at the point of vehicle/anti-solvent contact.

The term "vehicle" includes a single fluid or a mixture of two or more fluids, which are typically liquids but may be, for instance, supercritical or near-critical fluids. The fluids may be organic solvents or aqueous. In the case of a vehicle comprising two or more fluids, the overall mixture should have the necessary solubility and miscibility characteristics vis-à-vis the active substance, the additive and the anti-solvent fluid.

The vehicle or its component fluids may contain, in solution or suspension, other materials apart from the active substance and additive.

The selection of ail appropriate vehicle depends on the active substance, the additive and the anti-solvent fluid as well as on the chosen operating conditions (including pressure, temperature and fluid flow rates). Based on the above guidelines as to the miscibility and solubility characteristics of the fluids involved, the skilled person would be well able to select suitable materials with which to carry out the method of the invention.

When the vehicle is composed of two or more fluids, for instance an organic solvent with a minor amount of a co-solvent "modifier", or a water/organic solvent mixture, the two or more fluids may be mixed, so as to form the target solution, in situ, i.e., at or immediately before the target solution contacts the anti-solvent fluid and particle formation occurs. Thus, in one embodiment of the invention, the active substance is dissolved in a first fluid and the additive in a second fluid, and the first and second fluids are mixed, so as to form the target solution, at or immediately before the target solution contacts the anti-solvent fluid and precipitation occurs.

Figure 3:
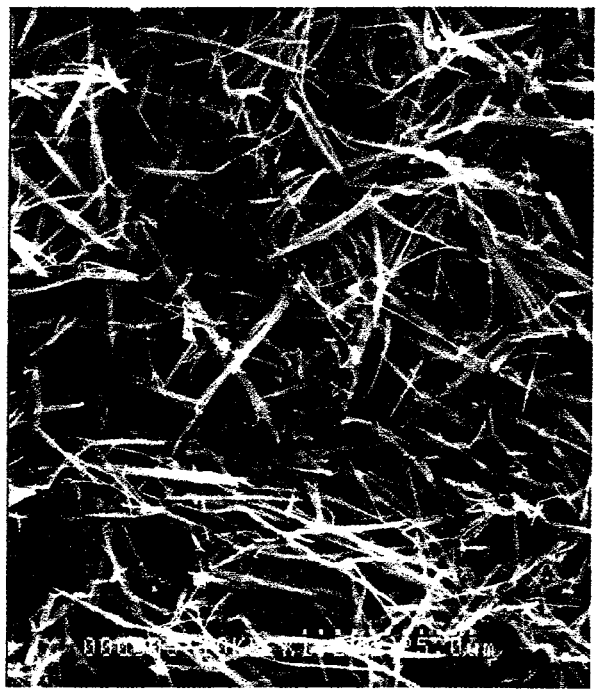
Figure 4:

Ideally this mixing of the vehicle fluids occurs at the outlet of a nozzle used to co-introduce the fluids into a particle formation vessel. For example, a first fluid in which the active substance is dissolved may be introduced through one passage of a multi-passage co nozzle as described in WO-96/00610 (FIGS. 3 and 4) or WO-01/03821 (FIG. 4). A second fluid, in which the additive is dissolved, may be introduced through another passage of the nozzle. The nozzle passage outlets may be arranged to terminate adjacent one another at the entrance to the particle formation vessel, in a way that allows the two fluids to meet and mix inside the nozzle, immediately before coming into contact with an anti-solvent fluid introduced through another nozzle passage. Both fluids will be extracted together into the anti-solvent fluid, resulting in co-precipitation of the active substance and the additive. For this to work, at least one of the vehicle fluids should be miscible, or substantially so, with the anti-solvent fluid. Ideally, although not necessarily (as described in WO-01/03821), the two vehicle fluids should be miscible or substantially miscible with one another.

Such in situ mixing of vehicle fluids may be particularly useful if there is no readily available common solvent for the active substance and the additive (for instance, when one material is organic and the other inorganic), or if the active substance and additive solutions are in some way incompatible, for instance if the active and additive would form an unstable solution mixture in a common solvent.

The anti-solvent fluid is a fluid, or a mixture of fluids, in which both the active substance and the additive are for all practical purposes (in particular, under the chosen operating conditions and taking into account any fluid modifiers present) insoluble or substantially insoluble. By "insoluble" is meant that the anti-solvent cannot, at the point where it extracts the vehicle, extract or dissolve the active substance or additive as particles are formed. Preferably the active substance and the additive are less than $10^{-5}$ mole %, more preferably less than $10^{-7}$ mole % or less than $10^{-8}$ mole %, soluble in the anti-solvent fluid.

The anti-solvent fluid should be a supercritical or near-critical fluid under the operating conditions used. By "supercritical fluid" is meant a fluid at or above its critical pressure ($P_c$) and critical temperature ($T_c$) simultaneously. In practice, the pressure of the fluid is likely to be in the range $(1.01-9.0)P_c$, preferably $(1.01-7.0)P_c$, and its temperature in the range $(1.01-4.0)T_c$ (where $T_c$ is measured in Kelvin). However, some fluids (e.g., helium and neon) have particularly low critical pressures and temperatures, and may need to be used under operating conditions well in excess of (such as up to 200 times) those critical values.

The term "near-critical fluid" encompasses both high pressure liquids, which are fluids at or above their critical pressure but below (although preferably close to) their critical temperature, and dense vapors, which are fluids at or above their critical temperature but below (although preferably close to) their critical pressure.

By way of example, a high pressure liquid might have a pressure between about 1.01 and 9 times its $P_c$, and a temperature between about 0.5 and 0.99 times its $T_c$, preferably between 0.8 and 0.99 times its $T_c$. A dense vapor might, correspondingly, have a pressure between about 0.5 and 0.99 times its $P_c$ (preferably between 0.8 and 0.99 times), and a temperature between about 1.01 and 4 times its $T_c$.

The anti-solvent is preferably a supercritical fluid such as supercritical carbon dioxide, nitrogen, nitrous oxide, sulfur hexafluoride, xenon, ethane, ethylene, chlorotrifluoromethane, chlorodifluoromethane, dichloromethane, trifluoromethane or a noble gas such as helium or neon, or a supercritical mixture of any of these. Most preferably it is supercritical carbon dioxide, ideally on its own rather than in admixture with other fluids such as supercritical nitrogen.

When carrying out the embodiments of the invention using a supercritical or near-critical fluid anti-solvent, the operating conditions must generally be such that the solution which is formed when the anti-solvent extracts the vehicle remains in the supercritical/near-critical form during the particle formation step. This supercritical/near-critical solution should therefore be above the $T_c$ and $P_c$ of the vehicle/anti-solvent mixture. This generally means that at least one of its constituent fluids (usually the anti-solvent fluid, which in general will be the major constituent of the mixture) should be in a supercritical or near-critical state at the time of particle formation. There should at that time be a single-phase mixture of the vehicle and the anti-solvent fluid, otherwise the particulate product might be distributed between two or more fluid phases, in some of which it might be able to re-dissolve. This is why the anti-solvent fluid needs to be miscible or substantially miscible with the vehicle.

The anti-solvent fluid may contain one or more modifiers, for example water, methanol, ethanol, isopropanol or acetone. A modifier (or co-solvent) may be described as a chemical which, when added to a fluid such as a supercritical or near-critical fluid, changes the intrinsic properties of that fluid in or around its critical point, in particular its ability to dissolve other materials. When used, a modifier preferably constitutes not more than 40 mole %, more preferably not more than 20 mole %, and most preferably between 1 and 10 mole %, of the anti-solvent fluid.

The anti-solvent flow rate will generally be chosen to ensure an excess of the anti-solvent over the target solution when the fluids come into contact, to minimize the risk of the vehicle re-dissolving and/or agglomerating the particles formed. At the point of its extraction the vehicle may typically constitute 80 mole % or less, preferably 50 mole % or less or 30 mole % or less, more preferably 20 mole % or less and most preferably 5 mole % or less, of the fluid mixture formed.

By "a SEDS™ particle formation process" is meant a process as described in WO-95/01221, WO-96/00610, WO-98/36825, WO-99/44733, WO-99/59710, WO-01/03821 and/or WO-01/15664, in which a supercritical or near-critical fluid anti-solvent is used simultaneously both to disperse, and to extract a fluid vehicle from, a solution or suspension of a target substance. Such a technique can provide better, and more consistent, control over the physicochemical properties of the product (particle size and size distribution, particle morphology, etc. . . . ) than has proved possible for coformulations in the past.

The simultaneous vehicle dispersion and extraction are preferably achieved by co-introducing the fluids into a particle formation vessel in such a way that the anti-solvent and the target solution both enter the vessel at the same point, which is substantially the same as the point where they meet and at which particle formation occurs. This is suitably achieved using a fluid inlet nozzle having two or more coaxial, concentric passages such as is shown in FIGS. 3 and 4 of WO-95/01221.

Because some embodiments of the invention are a modified version of those disclosed in the above listed patent publications, technical features of the processes described in those documents can apply also to embodiments of the invention. The earlier documents are therefore intended to be read together with the current application.

The concentration of the active substance and the additive in the target solution must be chosen to give the desired active:additive ratio in the final product. In the case of a crystalline or semi-crystalline active substance, it is preferred that their relative concentrations be such that the active is able to precipitate in a crystalline form under the operating conditions used (with some additives, in particular polymeric excipients, most particularly semi-crystalline and/or amorphous polymers, too high an additive level can force the active to precipitate in an amorphous form homogeneously dispersed throughout a "matrix" of the additive, with no outer coating). At the same time, the relative active and additive concentrations when carrying out embodiments of the invention are preferably such that there is sufficient additive to generate an additive-rich, preferably active-free or substantially so, layer at the particle surface (too low an additive level could be insufficient to achieve "coating" of all particles).

The additive level in the co-precipitated particles may be up to 50, 60, 70 or even 80% w/w. However, particularly preferred are relatively low levels of the additive, for instance 45% w/w or less, preferably 40% w/w or less, more preferably 30% w/w or less, most preferably 25% or 20% or 15% or 10% or 5% w/w or less. The active substance level is therefore, correspondingly, preferably 55% w/w or greater, more preferably 60% w/w or greater, most preferably 70% or 75% or 80% or 85% or 90% or 95% w/w or greater.

However, too low an additive concentration can be insufficient to form a protective surface layer around the active-rich particle core. The additive level may therefore be preferred to be at least 1%, preferably at least 2%, more preferably at least 5%, most preferably at least 10% or 20% w/w. For a taste masking additive, the level may be preferred to be at least 10% w/w, preferably at least 15% w/w, more preferably at least 20% or 25% or 30% or 40% w/w, of the overall composition. The amount needed for effective coating will depend to an extent on the size of the particles to be formed-smaller particles will have a higher surface area and thus require correspondingly higher additive levels.

Thus, preferred additive concentrations might be between 1% and 45% w/w, more preferably between 5% and 45% w/w, most preferably between 10% and 40% w/w or between 15% and 35% w/w.

An appropriate active:additive concentration ratio will usually manifest itself by a reduction in the crystallinity of a crystalline/semi-crystalline active substance, when coformulated in accordance with the invention, compared to its pure form, although not reduction to a completely amorphous phase. The ratio is preferably such that in the product coformulation, a crystalline or semi-crystalline active substance demonstrates between 20% and 95%, preferably between 50% and 90%, more preferably between 60% and 90% crystallinity as compared to the active starting material. This indicates a degree of active/additive interaction, but not a truly intimate solid dispersion.

It is thus possible to test for an appropriate active:additive concentration ratio, for a system containing a crystalline or semi-crystalline active substance, by preparing a range of samples with different ratios and identifying an upper limit in the additive concentration, above which the active crystallinity is too greatly disturbed (for example, less than 10% crystallinity, or 100% amorphous). A sensible additive level, below this limit, can then be found by identifying systems in which the active crystallinity is appreciably reduced (e.g., by at least 10% or preferably 20%, possibly by up to 30% or 40% or 50%).

Analysis by scanning electron microscopy (SEM) may suitably be used to establish the nature of the products tested; differential scanning calorimetry (DSC) and/or X-ray diffraction (XRD) may be used to investigate degree of crystallinity, typically by comparing with data from the pure, completely crystalline active starting material and also its totally amorphous form. Confocal Raman microscopy (for instance, using a system such as the HoioLab™ Series 5000) may also be used to establish whether a given product has the desired active/additive distribution—this builds up a "sectional" view through a particle and can reveal the nature and/or relative quantities of the substances present in the section scanned.

As well as the relative concentrations of the active substance and the additive, other parameters may be varied if necessary in order to achieve a coformulation in accordance with embodiments of the invention. Such parameters include the temperature and pressure at the point of particle formation, the concentrations of the active and additive in the target solution, the nature of the vehicle and of the anti-solvent fluid (taking account of any modifiers present) and their flow rates upon contact with one another.

It has not previously been recognized that a co-precipitation process performed using SEDS™, whatever the relative concentrations of the co-precipitated species, could ever result in a product in which there was both an intimate solid dispersion of the species and a coating effect of one species by the other, with no distinct phase boundary between the two regions.

The co-precipitated product of the method of the invention appears to be a type of solid dispersion, each particle containing a molecular-level mixture of both the active substance and the additive. However, it has surprisingly been found that the product is not a homogeneous mixture of the two components, but has a significantly lower level of the active substance at and near the surface of each particle compared to that in the particle core, sufficient for the additive to form, in effect, a protective surface layer. Thus, for example, a taste masking additive can mask even a strongly flavored active substance, while at the same time also being incorporated into the sub-surface core of each particle. There is typically, however, no distinct physical boundary between the protective surface "layer" and the "enclosed" core, but instead a gradual change, with a finite gradient, in the active:additive ratio. The particle constitution is that of a solid dispersion throughout, but with a varying additive concentration across its radius.

It has also, surprisingly, been found that for certain active/additive systems, in particular certain drug/polymer systems, SEDS™ coformulation does not readily yield an amorphous phase active, even up to in some cases 80% w/w additive. Instead the coformulated product can still contain crystalline active substance with a relatively high additive concentration at the particle surfaces.

The process of the invention works particularly well, it is believed (although we do not wish to be bound by this theory), when the active substance precipitates more quickly than the additive under the operating conditions (including choice of solid and fluid reagents) used. More specifically, this occurs when the nucleation and/or particle growth rate of the active substance is higher, preferably significantly higher, than that of the additive. The quicker growing active substance appears to precipitate initially as a "core" particle, around which both the active and the additive collect as the solid particles grow, with the relative concentration of the slower growing additive gradually increasing as the particles grow in diameter. Towards the outer surfaces of the particles, when most of the active present has already precipitated, the concentration of the additive becomes sufficiently high that it then effectively "coats" the active-rich core.

Thus, the operating conditions and/or the reagents used in the method of the invention should ideally be chosen so as to enhance or maximize the difference between the precipitation rates of the active substance and the additive. (By "precipitation rate" is meant the combined effects of the nucleation and particle growth rates.) This may in turn mean enhancing or maximizing the chance of phase separation occurring, between on the one hand the active substance and its associated vehicle and on the other hand the additive and its associated vehicle, immediately prior to or at the point of particle formation; phase separation can inhibit formation of a truly homogeneous solid dispersion between the active and additive.

Certain active/additive pairs will already have significantly different precipitation rates. This appears particularly to be the case when the active substance precipitates in a crystalline form and the additive in an amorphous form. Crystal habit may also affect the active substance precipitation rate. For example, it has been found that the invented process can be effective for active substances having a needle-like crystalline habit, possibly because the crystal growth rate is significantly faster in one dimension than in the others. Generally speaking, the active substance may have a crystalline form (under the conditions used) which is significantly longer in one dimension than in at least one other dimension, and/or its crystals may grow significantly faster in one dimension than in at least one other dimension; this embraces for example needle-like crystals and also, potentially, wafer- or plate-like crystals (for which growth is faster in two dimensions than in the third) and elongate prism-shaped crystals. Active substances having other crystal habits, or amorphous actives, may of course be protected using the method of the invention, using operating conditions suitable to enhance the difference between the active and additive precipitation rates.

In the above discussion, "significantly" longer or faster means approximately 5% or more, preferably at least 10% or 20% or 30%, greater than the length or speed of the lower of the two parameters being compared.

Embodiments of the invention may also be effective when the active substance and the additive have significantly different (for instance, at least 5% different, preferably at least 10%, more preferably at least 20% or 30%, based on the lower of the two values) solubilities in the anti-solvent fluid, as this can also affect the relative precipitation rates of the active and additive particles. This effect could be enhanced by the inclusion of suitable modifiers in the anti-solvent fluid, and/or by introducing a "secondary" anti-solvent fluid, having a lower capacity than the main anti-solvent for extracting the vehicle, as described in WO-99/44733. Generally, the additive should be more soluble than the active substance in the anti-solvent fluid, which should promote precipitation of the additive nearer to the particle surfaces.

Similarly, when the active substance and additive have a low compatibility with one another, i.e., a low solubility in or affinity for or miscibility with one another, this too can make them less likely to precipitate together in intimate admixture. For example, the active substance and additive will preferably have a solubility in one another of less than 30% w/w, more preferably less than 25% w/w, most preferably less than 20% or 15% or 10% w/w.

Thus, the active substance and additive might preferably have significantly different polarities and thus low mutual solubilities and a low mutual affinity—this is likely to reduce interaction between the active and additive during particle formation, and promote the growth of active-rich and additive-rich regions in the product particles.

Differences in polarity may be assessed for example by classifying each reagent as either polar, apolar, or of intermediate polarity. The polarity of a substance is something which can be assessed by the average skilled person by reference to the number, position and polarity of functional groups present on the substance, and can be affected by factors such as substituent chain lengths. Polar substances for instance typically contain a significant proportion of polar functional groups such as amine, primary amides, hydroxyl, cyano, carboxylic acid, carboxylate, nitrile, sulfoxide, sulfonyl, thiol, halide, and carboxylic acid halide groups, and other ionizable groups. Substances of medium polarity may contain functional groups of medium polarity, such as for instance esters, aldehydes, ketones, sulfides and secondary and tertiary amides. Substances of low polarity typically contain no functional groups or only functional groups of an apolar nature, such as alkyl, alkenyl, alkynyl, aryl and ether groups. Thus ethyl cellulose, for example, a polymer whose chain structure is dominated by alkyl groups, is considered to be non-polar, whereas the presence of a significant number of hydroxyl groups in hydroxypropyl methyl cellulose (HPMC) renders it a polar substance.

For polymers, polarity may also depend on the grade, for instance the molecular weight, degree of substitution, degree of cross-linking and any other co-monomers present.

Polar compounds include for instance acidic or basic compounds, ionic compounds, including salts, and otherwise highly charged species, vinyl polymers such as poly vinyl alcohol (PVA), HPMC as mentioned above, hydroxyethyl cellulose, hydroxypropyl cellulose, polyethylene glycols, polyacrylates and polymethacrylates and polyoxyalkylenes. Low polarity/apolar compounds include for example steroids, ethyl cellulose and lipidic materials. Materials of intermediate polarity include the polylactides and glycolides and mixtures thereof.

Assigning a value of 1, 2 or 3 to each reagent, 1 meaning low polarity or apolar, 3 meaning highly polar and 2 representing substances of intermediate polarity, it is preferred when practicing embodiments of the invention that the active substance and the additive have different polarity values. More preferably, the active has a polarity of 1 and the additive of 3, or vice versa.

It might previously have been expected that in such incompatible active/additive systems, a rapid solvent removal process such as SEDS™ would result in products containing two distinct phases, the active and additive precipitating separately from the fluid vehicle. Instead, it has surprisingly been found that SEDS™ may be used to generate a product having a gradual active/additive concentration gradient across it.

Instead or in addition, the operating conditions during the method of the invention may be modified to enhance the difference between the active and additive precipitation rates. Operating under relatively mild temperatures and/or pressures (for instance, only just above the critical temperature and/or pressure of the anti-solvent fluid (together with any modifiers which are present in it) may be expected to enhance any inherent differences in particle precipitation rates, by reducing the vehicle extraction rate and maximizing the chance of phase separation between the active and additive components.

Typically, such "mild" conditions might correspond to between 1 and 1.1 times the critical temperature $T_c$ (in Kelvin) of the anti-solvent fluid, preferably between 1 and 1.05 times $T_c$ or between 1.01 and 1.1 times $T_c$, more preferably between 1.01 and 1.05 times $T_c$ or between 1.01 and 1.03 times $T_c$. The pressure may be between 1 and 1.5 times the critical pressure $P_c$, preferably between 1.05 and 1.4 times $P_c$, more preferably between 1.08 or 1.1 and 1.35 times $P_c$. In the particular case of a carbon dioxide anti-solvent ($T_c$=304 K; $P_c$=74 bar), typical operating temperatures might be between 304 and 313 K, and operating pressures between 80 and 100 or 120 bar.

"Mild" working conditions may suitably be such that the anti-solvent fluid is in a supercritical form but more liquid-like than gas-like in its properties, i.e., its temperature is relatively close to (for instance, between 1 and 1.3 times) its $T_c$ (measured in Kelvin), but its pressure is significantly greater than (for instance, between 1.2 and 1.6 times) its $P_c$. Typically, for a supercritical carbon dioxide anti-solvent, the operating conditions are chosen so that the density of the anti-solvent fluid is between 0.4 and 0.8 g/cm$^3$, more preferably between 0.6 and 0.8 g/cm$^3$. Suitable operating conditions for a carbon dioxide anti-solvent are therefore between 25 and 50° C. (298 and 323 K), preferably between 32 and 40° C. (305 and 313 K), more preferably between 32 and 35° C. (305 and 308 K), and between 70 and 120 bar, preferably between 70 and 110 bar, more preferably between 70 and 100 bar.

Most preferred, when practicing embodiments of the invention, is to use an incompatible active/additive pair, as described above, and to carry out the particle formation under mild conditions, also as described above.

It can thus be important, when practicing the invention, to use a SEDS™ process but in doing so to seek to minimize the rate of vehicle extraction by the anti-solvent. This appears to make possible the gradual additive concentration gradient which is characteristic of products according to the invention. It is indeed surprising that a process such as SEDS™, which is known to involve an extremely rapid solvent removal, can nevertheless be used to coformulate reagents into products having a non-homogeneous active/additive distribution.

The rate of solvent extraction may be reduced in the ways described above, for instance by working under relatively "mild" conditions with respect to the critical temperature and pressure of the anti-solvent. Instead or in addition, the vehicle and the anti-solvent fluid may be chosen to have less than complete miscibility (i.e., to be immiscible in at least some relative proportions) under the chosen operating conditions, for instance to be less than very or freely soluble (e.g., as defined in the British Pharmacopoeia 1999, Volume 1, pages 11 and 21) in one another. For a carbon dioxide anti-solvent, suitable vehicles might include higher boiling solvents, such as with a boiling point of at least 373 K, for instance higher (such as $C_4$-$C_{10}$) alcohols such as butanol, dimethyl sulfoxide (DMSO), dimethyl formamide (DMF) and mixtures thereof. Other, lower boiling solvents such as lower alcohols (e.g., methanol, ethanol), ketones (e.g., acetone) and the like, including mixtures of such solvents, may also of course be used. The vehicle may if appropriate contain minor (e.g., 10% v/v or less) amounts of other solvents (which may include water) to modify its solubility characteristics.

A higher target solution flow rate, relative to that of the anti-solvent fluid, can also help to increase solvent extraction times. Suitably the fluid flow rates are selected so as to achieve, at the point of target solution/anti-solvent contact, a vehicle:anti-solvent mole ratio of between 5 and 20%, preferably between 5 and 10%. A suitable flow rate for a supercritical $CO_2$ anti-solvent, for instance, may be 20 mL/min, and the target solution flow rate may then suitably be 1 mL/min or greater.

Moreover, a target solution containing a semi-crystalline or in particular an amorphous additive will typically have a relatively high viscosity. This too can help to impede solvent removal, again slowing the particle formation process and allowing the active substance to precipitate more rapidly than the additive.

As described above, the method of the invention may be practiced using two separate vehicle fluids, one carrying the active substance and one carrying the additive, which contact one another only at or immediately before their point of contact with the anti-solvent fluid (i.e., the point of vehicle extraction and particle formation). If the two vehicle fluids have significantly different solubilities in the anti-solvent fluid, this can cause a small degree of phase separation at the point of particle formation, the extent of which depends, inter alia, on the time period between the vehicles mixing and their contact with the anti-solvent fluid (which in turn depends on the fluid flow rates and the internal geometry of the fluid inlet used), and again can lead to differences in precipitation rate between the active and the additive.

Generally speaking, any difference in the rate of vehicle extraction, by the anti-solvent fluid, between the active substance containing solution and that carrying the additive, is thought to be able to increase the effectiveness of embodiments of the invention. The rate of vehicle extraction is in turn influenced by the molecular interactions between each solute and its respective solvent, high levels of interaction being likely to slow solvent extraction and inhibit precipitation. Thus, in this version of the invention, the solubility of the active substance in its vehicle fluid should be significantly (for instance, 5% or more, preferably at least 10% or 20% or 30%, based on the lower of the two solubilities) different to the solubility of the additive in its vehicle fluid. The active substance should ideally be less soluble in (i.e., form weaker interactions with) its (first) vehicle fluid than the additive is in its (second) vehicle fluid, so that the additive is marginally less ready to precipitate than the active.

Modifiers (co-solvents) in one or more of the vehicle fluid(s) and/or the anti-solvent fluid may be chosen to enhance such effects; operating pressures and temperatures, and even fluid flow rates, may also influence them.

The method of the invention preferably involves selecting the reagents (i.e., the active substance, the additive, the vehicle fluid(s), the anti-solvent fluid and any modifiers or co-solvents present) and the operating conditions (such as temperature and pressure at the point of particle formation, fluid flow rates and concentrations of the active and the additive in the vehicle), in order to increase the difference in particle precipitation rates, under the conditions used, between the active substance and the additive. Preferably the precipitation rate difference is at least 5% of that of the slower precipitating material more preferably at least 10%, most preferably at least 20% or 30% or 40% or 50% or 75% or 90% or 100%.

It can be seen from the above that there are several potential ways in which the precipitation rate difference may be enhanced or maximized in accordance with the invention.

The method of the invention can provide significant advantages over known methods for coating an active substance with an additive. Because it involves particle formation by SEDS™ it is a one-step process, which can be carried out in a closed environment, shielded if necessary from light, oxygen and other contaminants, and it allows excellent control over the physicochemical characteristics of the product (such as particle size and size distribution, morphology, purity, yield and handling properties), as described in the prior art on SEDS™. It is also extremely useful for formulating small particles, which can otherwise be difficult to coat.

The coformulated particles made according to the invention differ from conventional coated products; they are solid dispersions of one material in another, but with a finite gradient in the relative concentration of the additive, which concentration increases radially outwards from the core to the surface of each particle. The particles are thus (in particular at their surfaces) not truly homogeneous mixtures of the two components, such as one would expect from a prior art coformulation process, since such mixtures would include at least some exposed active substance at the particle surfaces and hence be unsuitable for protecting or masking the active substance. In particles made according to embodiments of the invention, the active substance:additive ratio, at the particle surface, can be sufficiently low for a taste masking additive to mask, effectively, the flavor of for example an extremely bitter tasting drug such as quinine sulphate.

Nor, however, are the particles "coated", in the conventional sense of the word, with the additive. They tend not to possess a core and a separate coating layer with a distinct physical boundary (at which boundary the "gradient" in the additive concentration is theoretically infinite) between them. Rather, they exhibit a gradual change from an active-rich core to an additive-rich (and preferably active-free) surface.

It is possible that the active substance at the core of a particle according to the invention will interact to at least some degree with the additive present in the particle, and towards the centre the particle may have the form of a solid dispersion of the active and additive, manifested in general by a disturbance in the crystallinity of a crystalline or semi-crystalline active even at the particle core. However it is also possible that a particle may be formed in which, at its centre, the active exists in a pure (and if relevant, crystalline) form. Evidence to date (in particular Raman confocal microscopy studies) suggest that a particle made by the method of the invention does not exhibit more than one separate "phase" nor any distinct phase boundary, but rather contains only gradual transitions between regions of different active:additive concentration ratios across its diameter.

Such particle properties, thought to be unique, are likely to influence their dissolution profiles, in particular where the additive acts to inhibit release of the active substance. The release-inhibiting effect is likely to be most marked during an initial period of time corresponding to dissolution of the additive at the particle surfaces, and to falloff gradually thereafter.

Differential scanning calorimetry (DSC) data from the products is also likely to be affected by their unique active: additive concentration profile. For instance, when the active substance is crystalline or semi-crystalline, it is expected that the DSC profile for a product made according to the invention will exhibit one or more peaks indicative of crystalline active, but that the peak(s) will be broader to at least some degree than those for the pure active substance, indicating a degree of interaction between the active and the additive. When both the active and the additive are crystalline or semi-crystalline, it can be expected that the DSC profile of the coformulation will exhibit two distinct peaks or sets of peaks, one for the active substance and one for the additive, with both peaks/sets being broader than those for the pure starting materials, again indicating a degree of solid/solid interaction but retention of at least some of the character of the individual materials.

Similarly, X-ray diffraction (XRD) analysis of a product made according to the invention is likely to indicate reduced crystallinity for a normally crystalline active substance, due to interaction with the additive, but not a completely amorphous system such as might be seen with a truly homogenous solid dispersion.

The gradient in the relative additive concentration, across the particle radius, will depend on a number of factors such as the solubility characteristics of the species present, the viscosities of their solutions, the nature and rate of their particle growth, etc., as described above. The gradient mayor may not be constant across the radius, but the rate of change in additive concentration is typically continuous rather than stepped, from the core to the additive-rich surface (which preferably contains, at its outer limit, 100% additive). It may be possible to identify "core" and "surface" regions of the particles with a concentration gradient between them. In this case the constitution of the "core" is preferably between 90 and 100% w/w active substance, more preferably between 95 and 100%, most preferably between 98 and 100% w/w (it is possible that the core will contain no additive at all).

The active substance in the core is preferably in a crystalline form, for instance between 80% and 100% or between 90 and 100%, ideally 100% crystalline.

The "surface" layer preferably contains between 5 and 0%, more preferably between 2 and 0% or between 1 and 0% or between 0.5 and 0%, most preferably 0% w/w of the active substance, i.e., there is preferably no active substance exposed at the outer particle surface.

For these purposes, the "surface" layer may suitably be taken to be the outermost region containing 0.0001% or more of the total particle volume, preferably 0.001% or more. The "core" region may suitably be taken to be the central region containing 0.0001% or more of the total particle volume, more preferably 0.001% or more. Either region may be taken to contain up to 0.01%, 0.1%, 1%, 5%, 10% or even 15% of the total particle volume.

The active:additive concentration gradient can be controlled, in the method of the invention, by altering the operating conditions as described above. It will be affected by these and by the nature of in particular the active substance and the additive but also the vehicle and the anti-solvent fluid. The skilled person, using available data on the solubilities, miscibilities and viscosities of the reagents he uses, should be well able to select and alter the operating conditions to influence the distribution of the additive in the product particles.

The degree of crystallinity of a normally crystalline active substance will also vary gradually from the core to the surface of the particle. At the centre, the active substance may be highly, possibly even 100%, crystalline, but towards the surface its interaction with the additive will typically be such as to disrupt its crystallinity and increasingly high levels of amorphous phase active substance may be present as the particle surface is approached. It can often be desirable, in for instance drug/excipient formulations, for an active substance to be present in a more readily dissolvable (and hence more bioavailable) amorphous form; this characteristic of the products of the invention can thus be advantageous, particularly when combined with the coating effect which can mask unpleasant flavors and/or delay release of the active substance for a desired period of time.

According to a second aspect of embodiments of the invention, there is provided a particulate coformulation of an active substance and a (typically protective) additive, of the type described above. The coformulation is a solid dispersion of one component in the other but with a finite gradient in the relative additive concentration which increases radially outwards from the core to the surface of the particles, the particles having an additive-rich surface region but preferably no distinct physical boundary between that region and the rest of the particle.

A particulate coformulation in accordance with the invention may alternatively be described as an intimate, molecular level, solid-phase mixture of an active substance and an additive, the particles of which have an additive-rich, preferably active substance-free, surface region. The active substance:additive ratio, at the particle surface, is preferably sufficiently low for the additive to form, effectively, a protective surface layer around the active substance.

In the case where the active substance has an unpleasant flavor or odor and the additive is a taste masking agent, the active substance:additive weight ratio, at the particle surfaces, is preferably sufficiently low for the additive to mask, effectively, the flavor or odor of the active substance.

The outer additive layer is preferably sufficient to prevent any detectable release of the active substance for at least 30 seconds, preferably at least 60, more preferably at least 90 or 120 or 150 or 180 or even 240 or 300 seconds after the product of the invention comes into contact with saliva in a consumer's mouth (or on immersion of the product in a pH neutral aqueous solution). It may also be preferred for there to be no detectable release of the active substance for at least 2, more preferably 3 or even 4 or 5, minutes on immersion of the product in an aqueous solution of pH between 1 and 2, mimicking the conditions in a consumer's stomach.

The thickness of the outer additive ("coating") layer will depend on the nature of the active and additive, the size of the particle as a whole and the use for which it is intended. Suitable outer layers might be between 0.1 and 10 μm in depth, more preferably between 0.1 and 5 μm.

A coformulation according to the invention preferably consists essentially of the active substance and the additive, i.e., it preferably contains no, or only minor amounts (for instance, less than 5% w/w, preferably less than 2% w/w or less than 1% w/w) of, additional ingredients such as surfactants, emulsifiers and stabilizers. It preferably contains no bulking agents such as silica, in particular colloidal silica.

A coformulation according to the second aspect of the invention is preferably made by a method according to the first aspect. Aspects of the coformulation such as the nature, amounts and distribution of the active substance and the additive are therefore preferably as described above in connection with the first aspect of the invention. The coformulation may in particular be or comprise a pharmaceutical or nutraceutical agent or a foodstuff. The active substance is preferably present in a crystalline form and the additive in an amorphous form.

The coformulation may have a particle volume mean diameter (in the case of spherical or approximately spherical particles) of between 0.5 and 100 μm, preferably between 0.5 and 20 μm, more preferably between 0.5 and 10 μm or between 1 and 10 μm. In the case of needle-like particles, the volume mean particle length is typically between 5 and 100 μm, preferably between 10 and 100 μm, more preferably between 50 and 100 μm, and the volume mean thickness between 0.5 and 5 μm, preferably between 1 and 5 μm. In the case of plate-like particles, the volume mean thickness is typically between 0.5 and 5 μm. Embodiments of the invention can thus be of particular benefit in preparing small particles having an effective coating deposited on them, since using conventional coating technologies the coating of fine particles (for instance, of size below 10 μm or 5 μm or more particularly below 1 μm) can be extremely difficult. Embodiments of the invention allow both core and coating to be generated in a single processing step, with a high level of control over product characteristics such as size and size distribution.

A third aspect of an embodiment of the invention provides a pharmaceutical composition which includes a coformulation according to the second aspect. The composition may be, for example, a tablet or powder, a suspension or any other dosage form, in particular one intended for oral or nasal delivery.

A fourth aspect of the invention provides a foodstuff or nutraceutical composition which includes a coformulation according to the second aspect.

A fifth aspect provides the use of a SEDS™ co-precipitation process in preparing particles of an active substance having a layer of an additive on the particle surfaces. By "co-precipitation process" is meant a method which involves dissolving both the active substance and the additive in a vehicle to form a single target solution, and contacting the target solution with an anti-solvent fluid so as to cause the active substance and additive to co-precipitate.

According to this fifth aspect of the invention, the SEDS™ co-precipitation is used to achieve a coating of the additive at the particle surfaces. Preferably the coating is a protective layer, in particular a taste and/or odor masking layer. A SEDS™ co-precipitation (i.e., both active and additive being precipitated together from a common solvent system) has not previously been used for such a purpose.

Some embodiments of the invention will now be described, by way of example only, with reference to the accompanying illustrative drawings, of which:

Experimental Examples A

These examples demonstrate the coformulation, using SEDS™, of the highly polar anti-malarial drug quinine sulphate (QS) (Sigma™, UK) with the apolar polymer ethyl cellulose (EC-N7, Hercules™, UK). QS has an unpleasant bitter taste and would conventionally need to be coated with a taste masking agent prior to administration.

A SEDS™ process was used to precipitate both drug and polymer together from a single "target solution". The apparatus used was analogous to that described in WO-95101221 (FIG. 1), using a 50 mL Keystone™ pressure vessel (available from Keystone Scientific, Inc., located in Bellefonte, Pa.) as the particle formation vessel and a two-passage concentric nozzle of the form depicted in FIG. 3 of WO-95/01221. The nozzle outlet had an internal diameter of 0.2 mm. Supercritical carbon dioxide was the chosen anti-solvent. The particle formation vessel was maintained at 100 bar and 35° C.

Example A1—Precipitation of QS Alone

A 1% w/v solution of QS in absolute ethanol was introduced into the particle formation vessel at 0.3 mL/min through the inner nozzle passage. Supercritical carbon dioxide was introduced at 9 mL/min through the outer nozzle passage. Particles formed and were collected in the vessel.

Figure 2:

The product was a fine, fluffy white powder. SEM (scanning electron microscope) examination showed a needle-like morphology (FIG. 1), different to that of the starting material (FIG. 2).

Example A2—Co-Precipitation of QS and Ethyl Cellulose

A 1% w/v solution of QS in absolute ethanol, also containing 20% by weight (based on the overall drug/polymer mix) of ethyl cellulose, was introduced into the particle formation vessel with supercritical carbon dioxide, using the same operating temperature and pressure, and the same fluid flow rates, as for Example A1.

The product, collected in the vessel, was again a fine, fluffy white powder, having a similar particle morphology to the product of Example A1 (see the SEM photograph in FIG. 3).

Examples A3-A10—Increasing the Polymer Concentration

Example A2 was repeated but using 5%, 10%, 30%, 40%, 50%, 60%, 70% and 80% w/w respectively of the ethyl cellulose polymer.

Figure 5:
Figure 6:

All products were fine, fluffy white powders. Those of Examples A3-A7 (respectively 5%, 10%, 30%, 40% and 50% w/w ethyl cellulose) had a needle-like particle morphology with smooth surfaces—see the representative SEM photographs in FIGS. 4, 5 and 6 for the products of Examples A3, A4 and A6 respectively.

Figure 7:

The Example A8 product (60% w/w ethyl cellulose) contained spherical particles, most likely of ethyl cellulose, deposited on the edges of needle-like particles (see FIG. 7). This effect became more marked as the ethyl cellulose content increased, the spherical polymer particles covering almost all the QS crystal surfaces in the products of Examples A9 (70% w/w ethyl cellulose, FIG. 8) and A10 (80% w/w ethyl cellulose, FIG. 9).

Results and Discussion

Figure 10:
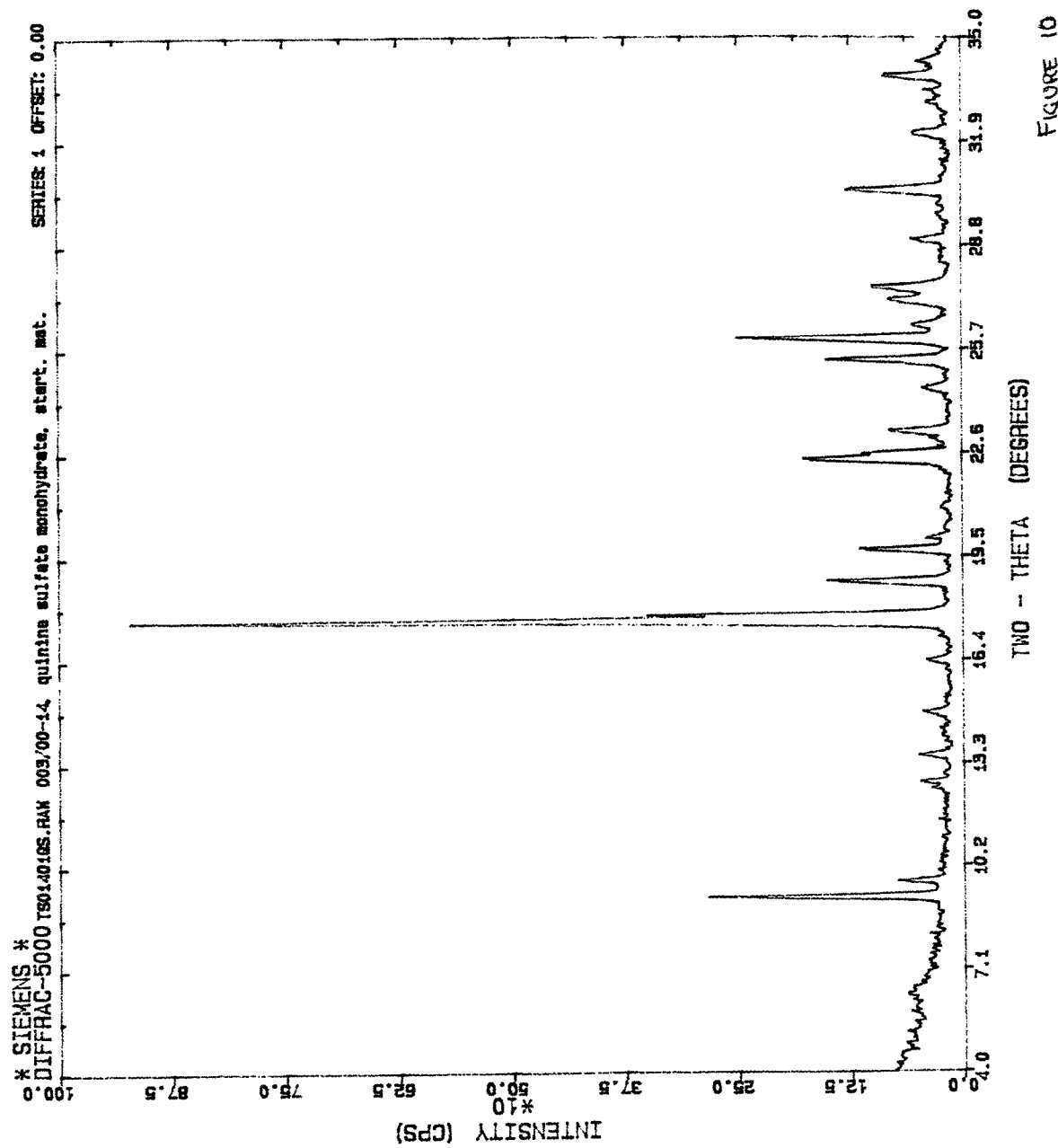
FIGS. 10-12 are X-ray diffraction (XRD) patterns for pure quinine sulphate and the products of Examples A6 and A8 respectively.
Figure 11:
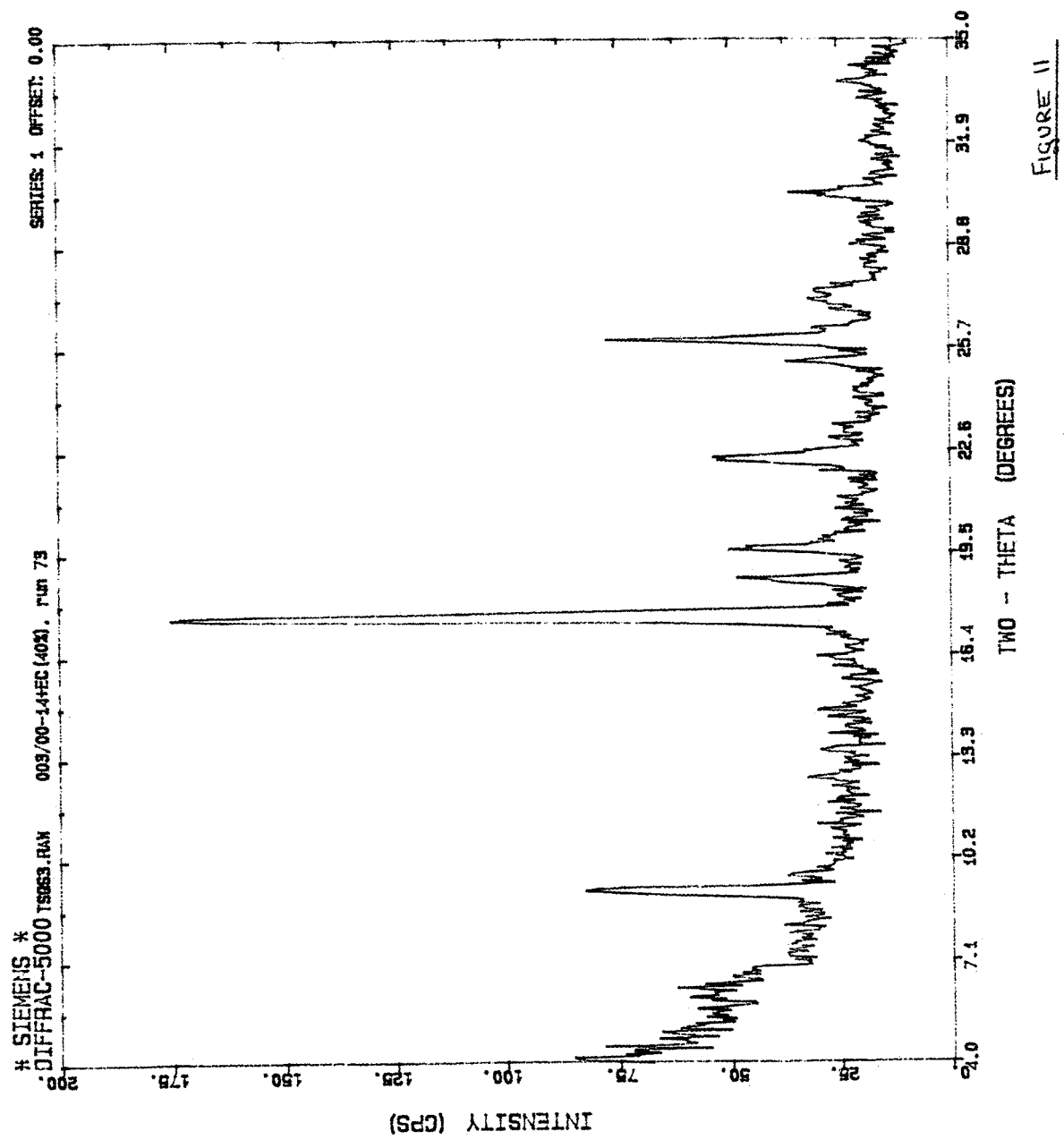
Figure 12:
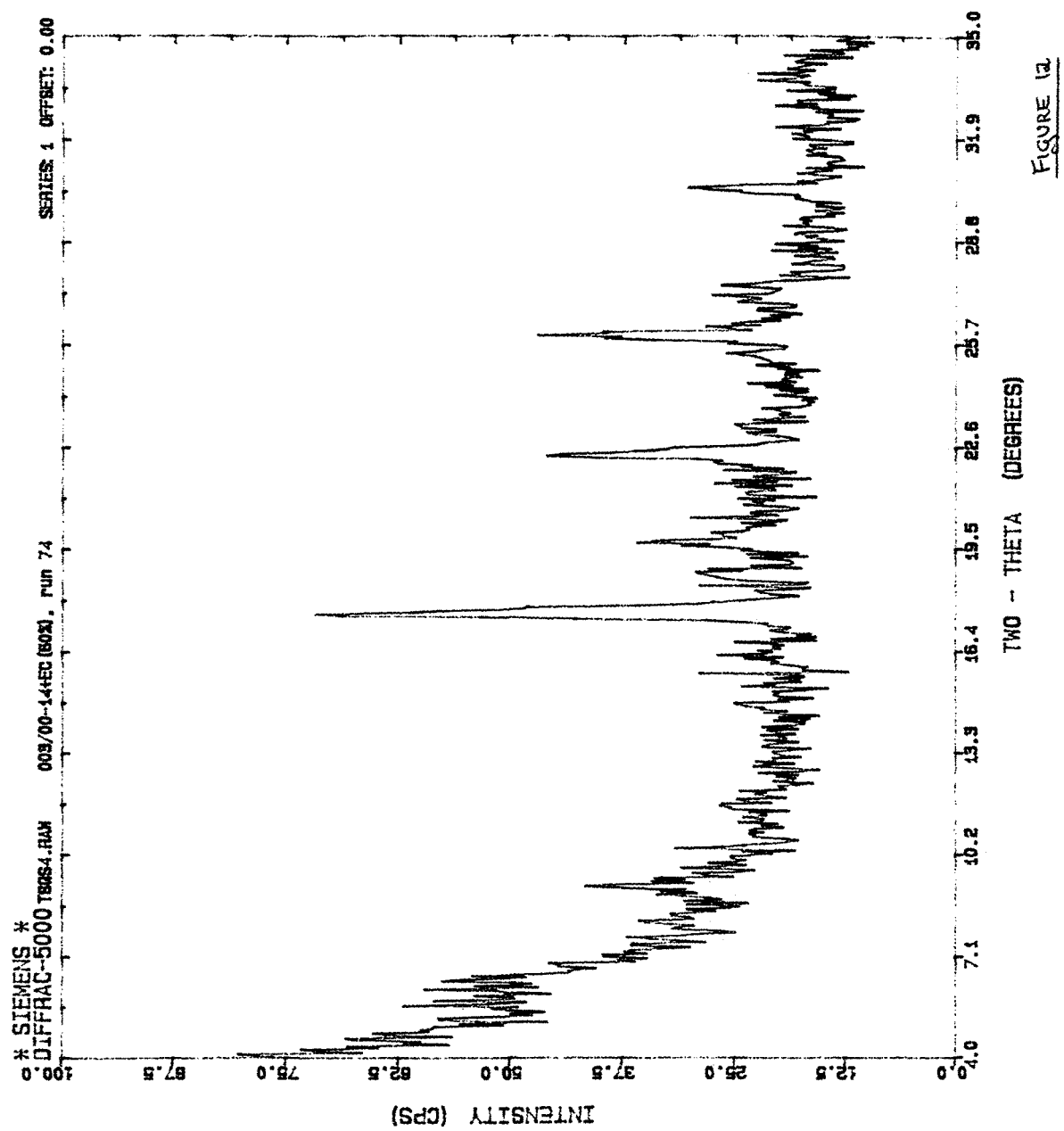

The X-ray diffraction (XRD) patterns for the products of Examples A2 to A10 were essentially similar (in terms of peak positions) to that of the pure, unprocessed QS powder (FIG. 10). This indicates that there had been no solid state phase (polymorphic) change in the QS during SEDS™ processing and that its crystalline phase was still present in all products. In other words, the products were not true solid "dispersions" of the drug in the polymer (as were, for example, the products described in WO-01/15664). FIGS. 11 and 12 show the XRD patterns for the products of Examples A6 and A8 respectively; a slight reduction in crystallinity can be observed, which is consistent with the presence of the polymer in the surface regions of the particles.

The XRD data are also consistent with the SEM observations of crystalline particles with polymer-like features on the particle surfaces.

When co-formulating a drug with more than about 40% w/w of a polymer, in general an amorphous particulate product would be expected. Typically, even at levels below 40% w/w, the presence of the polymer would still be expected to cause a substantial decrease in the degree of drug crystallinity. This is illustrated and confirmed by the teachings in WO-01/15664. It is therefore surprising to find that the products of the present examples retained a substantial degree of crystallinity, even in those containing as much as 60% w/w (FIGS. 7 and 12) or 80% w/w (FIG. 9) of the polymer. It is thought that this could be due to the difference in the rate of solvent extraction, by the supercritical carbon dioxide, from the solution elements of on the one hand the drug and on the other the polymer, under the relatively mild working conditions used. Relatively high levels of interaction between the polymer and the ethanol solvent, as compared to those between the QS and the ethanol, combined with relatively low levels of interaction between the polar drug and the hydrophobic polymer, could cause slower solvent extraction in the region of the polymer molecules, and hence delay or discourage their precipitation.

On tasting the products of Examples A5 to A10 (by four panelists), no bitterness could be detected for up to as long as 120 seconds or more. In contrast, pure QS gave an immediately detectable bitter taste. This indicates that, at least at the particle surfaces in the coformulated products, there was no available QS and an extremely high (perhaps 100%) concentration of ethyl cellulose. That this can be achieved even at up to 70% w/w QS (Example A5) could be of significant benefit in the formulation of quinine sulphate dosage forms.

Figure 8:
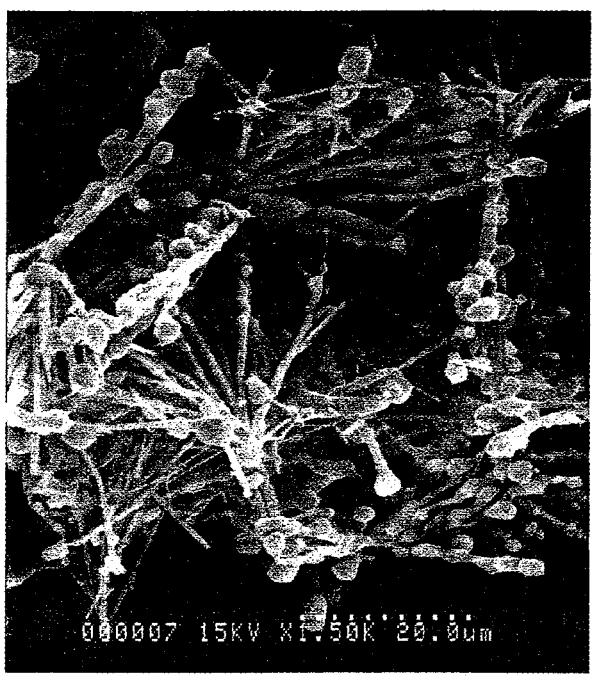
Figure 9:
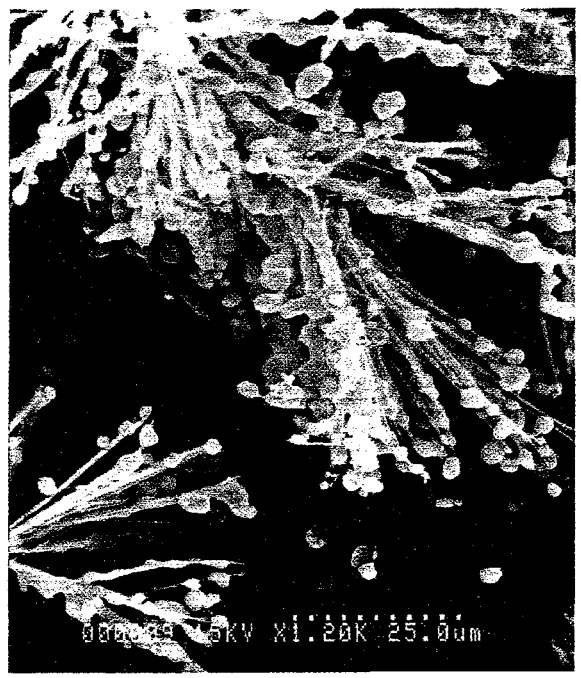

These tasting experiments, although not rigorous, provide an effective indication of the existence of a continuous protective layer, analogous to a coating, at the particle surfaces, an unexpected result from a coformulation process. It appears that this continuous layer is present in addition to the separate particles of excess polymer which are visible on the crystal surfaces in the Example A8 to A10 products (FIGS. 7 to 9).

Experimental Examples B

These examples demonstrate the coformulation, using SEDS™, of the artificial sweetener aspartame (L-aspartyl- L-phenylalanine methyl ester, Aldrich™, UK) with ethyl cellulose (EC-N7, Hercules™, UK). Aspartame is an intensely sweet chemical, having a sweetening power of approximately 180 to 200 times that of sucrose, which is widely used in beverages, table-top sweeteners and other food and nutraceutical (for instance, vitamin preparations) products. It was chosen for these experiments because of the ease with which it can be detected if insufficiently taste masked.

The aspartame (polar) and ethyl cellulose (non-polar) were precipitated together from a single "target solution" in a 1:1 v/v acetone:methanol solvent mixture. The apparatus and operating conditions (temperature, pressure and fluid flow rates) used were the same as those in Examples A. Again the anti-solvent was supercritical carbon dioxide.

Example B1—Co-Precipitation of Aspartame and Ethyl Cellulose

Figure 13:
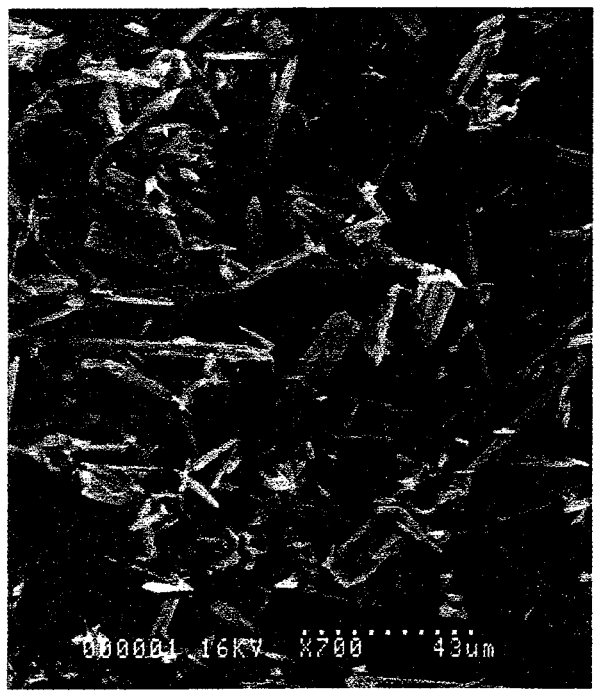
FIGS. 13-19 are SEM photographs of some of the products and starting materials for Examples B1 to B3, C1 and C2 below.
Figure 14:
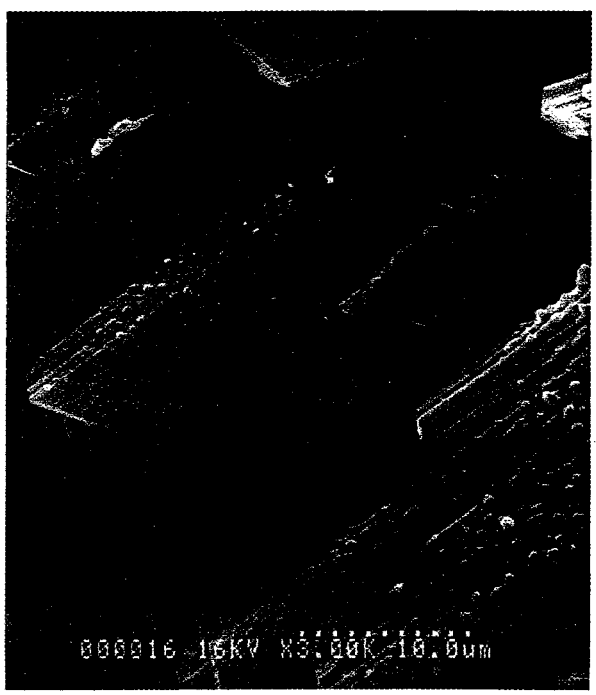

The target solution contained 1% w/v aspartame and 10% w/w ethyl cellulose. The product collected in the particle formation vessel was a fine, fluffy white powder. SEM examination showed a needle-like morphology (FIG. 14), similar to that of the aspartame starting material (FIG. 13), but with small spherical polymer particles visible on the aspartame crystal surfaces even at this relatively low polymer concentration.

Examples B2 and B3—Increasing the Polymer Concentration

Figure 15:
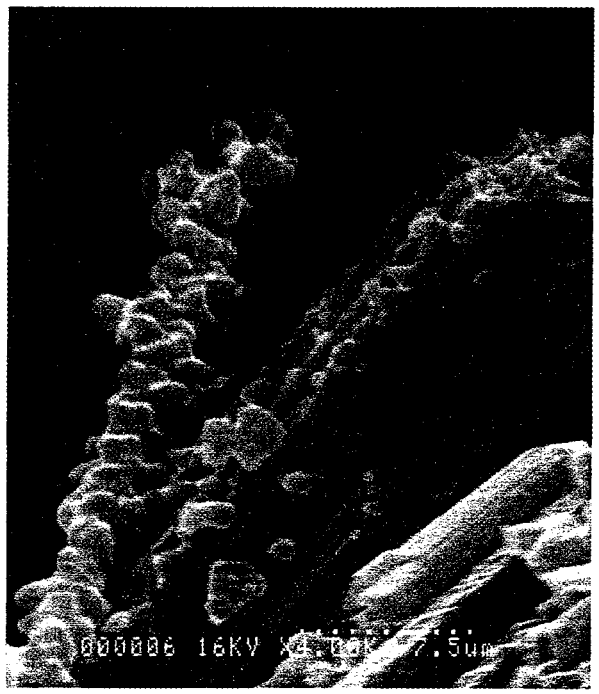
Figure 16:
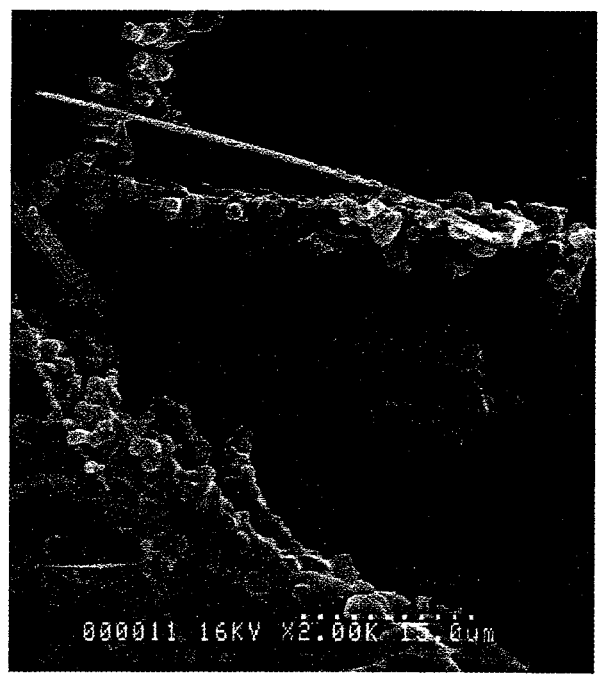

Example B1 was repeated but with ethyl cellulose concentrations of 30 and 60% w/w respectively in the target solution. In both cases the product was a fine, fluffy white powder with similar morphology to that of Example B1, although at these levels the polymer particles appeared completely to cover the aspartame crystals. FIG. 15 is an SEM photograph of the Example B2 product (30% w/w ethyl cellulose); FIG. 16 shows that of Example B3 (60% w/w ethyl cellulose).

The Example B2 product (30% w/w ethyl cellulose) was tasted by seven panelists. No sweetness was detected for more than 600 seconds. In contrast, sweetness could be detected immediately from the as-supplied aspartame starting material. The taste masking effect is believed to be due to the hydrophobic ethyl cellulose layer covering virtually every aspartame particle (FIG. 15).

Experimental Examples C

In these experiments, the method of the invention was used to apply a taste masking coating to a highly polar active substance (NaCl) precipitated from an aqueous solution. Two alternative processing methods were used (Experiments C1 and C2). The products of both experiments were tasted by five panelists. Very little if any saltiness was detected for more than 300 seconds, indicating efficient coating of the NaCl with the taste masking additive.

These results illustrate further the broad applicability of embodiments of the invention.

Example C1—In Situ Mixing of Active and Additive Solutions

A three-passage coaxial nozzle, of the type illustrated in FIG. 3 of WO-96/00610, was used to co-introduce into a 50 mL Keystone™ pressure vessel (a) a 30% w/v solution of pure NaCl (>99%, Sigma™ UK) in deionized water, (b) a 0.22% w/v solution of EC-N7 (as in Examples B) in pure methanol and (c) supercritical carbon dioxide as the anti-solvent. The NaCl and EC-N7 solutions, introduced through the intermediate and inner nozzle passages respectively, met inside the nozzle immediately prior to their contact with carbon dioxide flowing through the outer nozzle passage.

The flow rates for the fluids were (a) 0.02 mL/min, (b) 1.2 mL/min and (c) 36 mL/min. The pressure vessel was maintained at 100 bar and 35° C. The nozzle outlet had an internal diameter of 0.2 mm.

Figure 17:
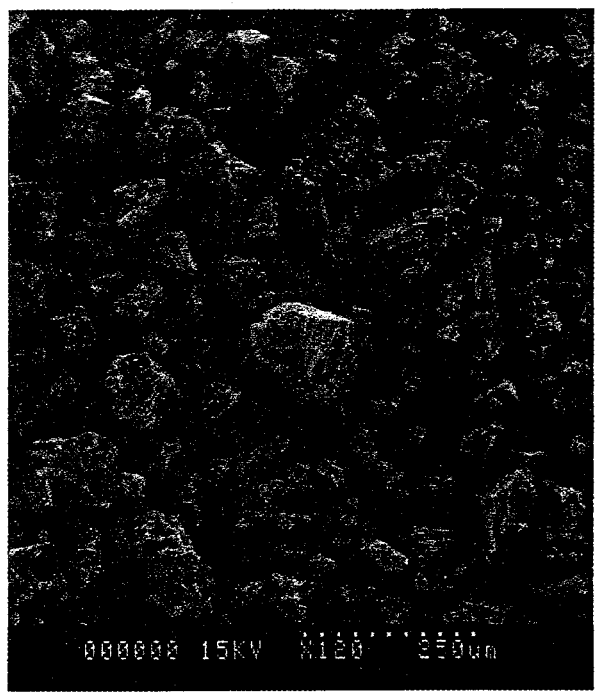
Figure 18:

The relative NaCl and EC-N7 concentrations yielded a coformulation containing 30% w/w of the ethyl cellulose. The product was a fine, fluffy, white powder; SEM analysis showed microparticles with a rounded morphology (FIG. 18) which were much smaller than those of the as received, milled pure NaCl (FIG. 17).

Figure 20:
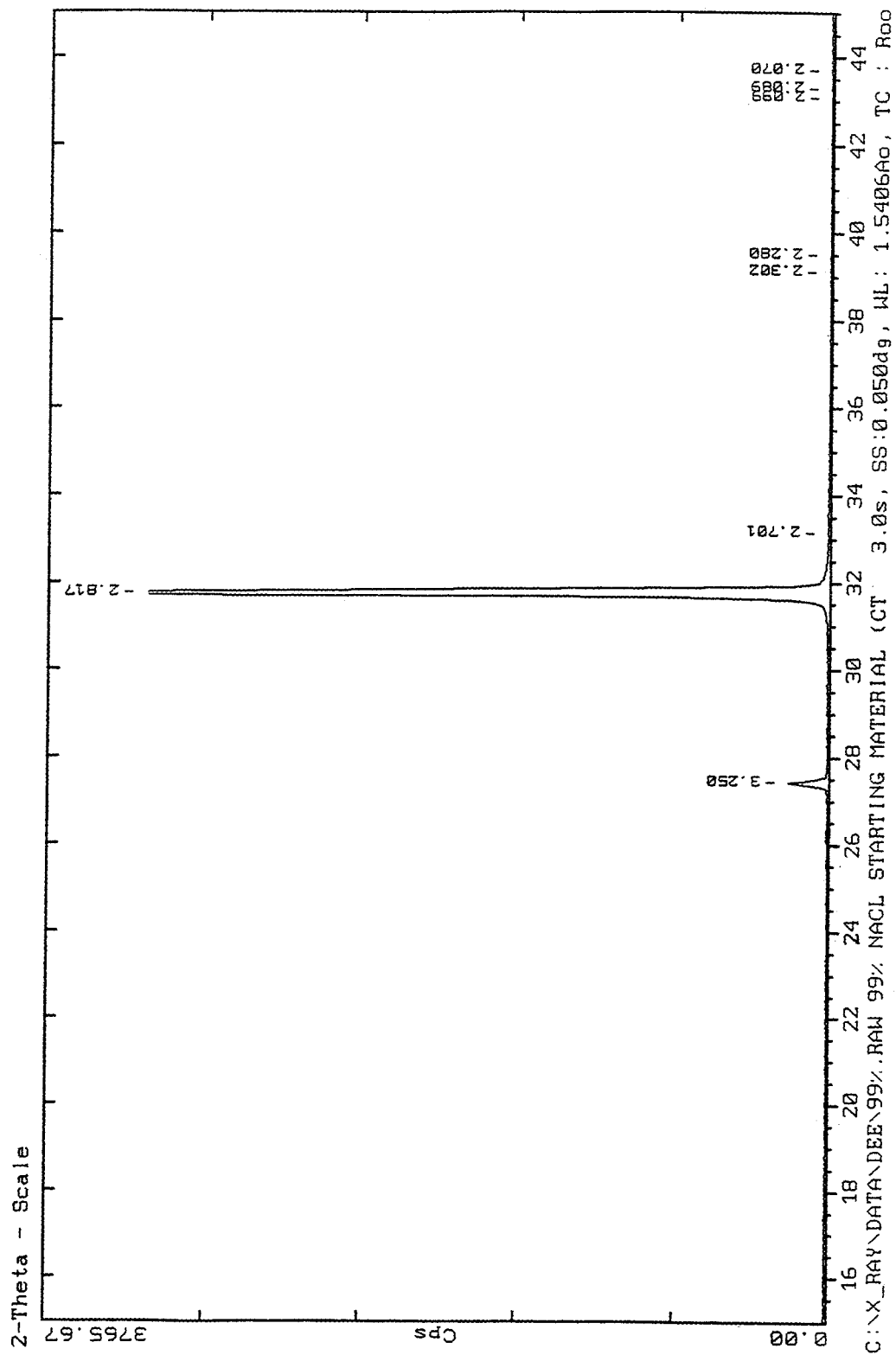
FIGS. 20-21 are XRD patterns for pure sodium chloride and the product of Example C1 respectively.
Figure 21:
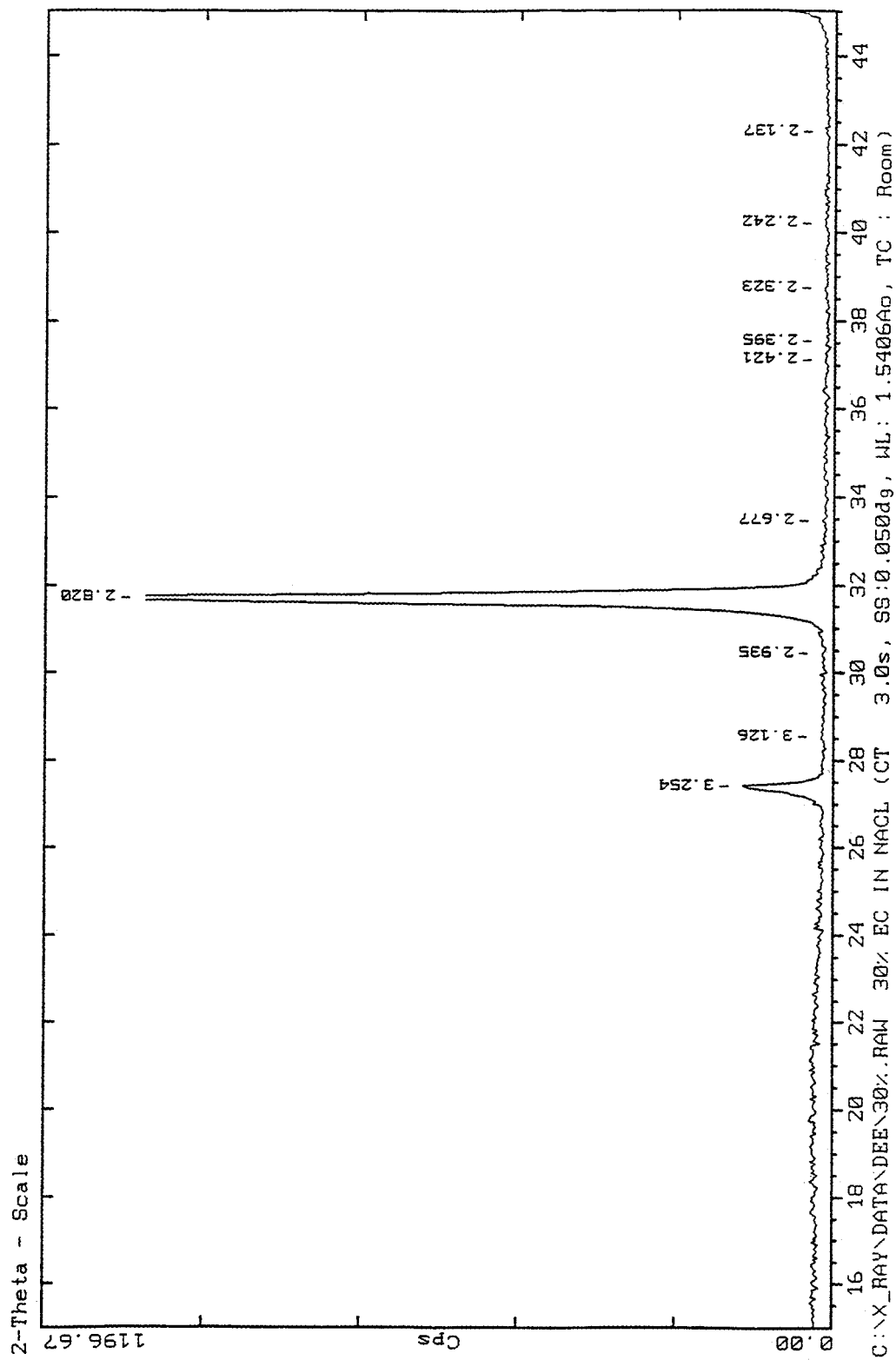

FIGS. 20 and 21 are XRD patterns for the NaCl starting material and the Example C1 product respectively. That for the C1 product indicates a slight reduction in crystallinity compared to that for the starting material, due to the presence of the polymer.

Example C2—Pre-Mixing of Active and Additive Solutions

In this experiment, 0.3 g of pure NaCl was dissolved in 1 mL of deionized water to form solution A, 0.13 g of EC-N7 was dissolved in 60 mL of pure methanol to form solution B. Solution B was then added to solution A to form a solution mixture C. Mixture C was then pumped at 0.3 mL/min into a 50 mL Keystone™ vessel kept at 100 bar and 35° C., via the inner passage of a two-passage coaxial nozzle (outlet diameter 0.2 mm) as used in Examples B. Supercritical carbon dioxide was introduced at 9 mL/min through the outer nozzle passage.

Figure 19:
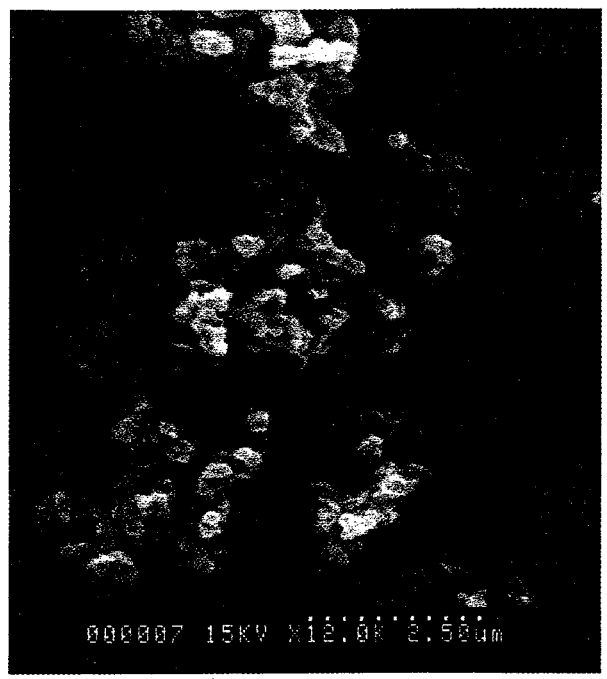

The product was a fine, fluffy white powder (SEM photomicrograph shown in FIG. 19) having a similar morphology to that of the Example C1 product.

Experimental Example D—Product Characterization

In this example, the constitution of a product prepared according to the invention was analyzed.

The product contained 20% w/w quinine sulphate (QS) with an ethyl cellulose (EC) coating agent. It was prepared in the same way as Examples A, using the same operating temperature, pressure and fluid flow rates and the same two-passage coaxial nozzle. Supercritical carbon dioxide was the anti-solvent and the drug and coating agent were dissolved in absolute ethanol at 1% w/v.

The product was analyzed by Raman spectroscopy using the Kaiser™ Raman confocal microscope system (Holo-Lab™ Series 5000). This builds up a cross-sectional image of the constitution of the product particles. The laser power at the sample was approximately 27 mW at 785 nm from an attenuated Kaiser™ Invictus™ diode laser.

Figure 22B:
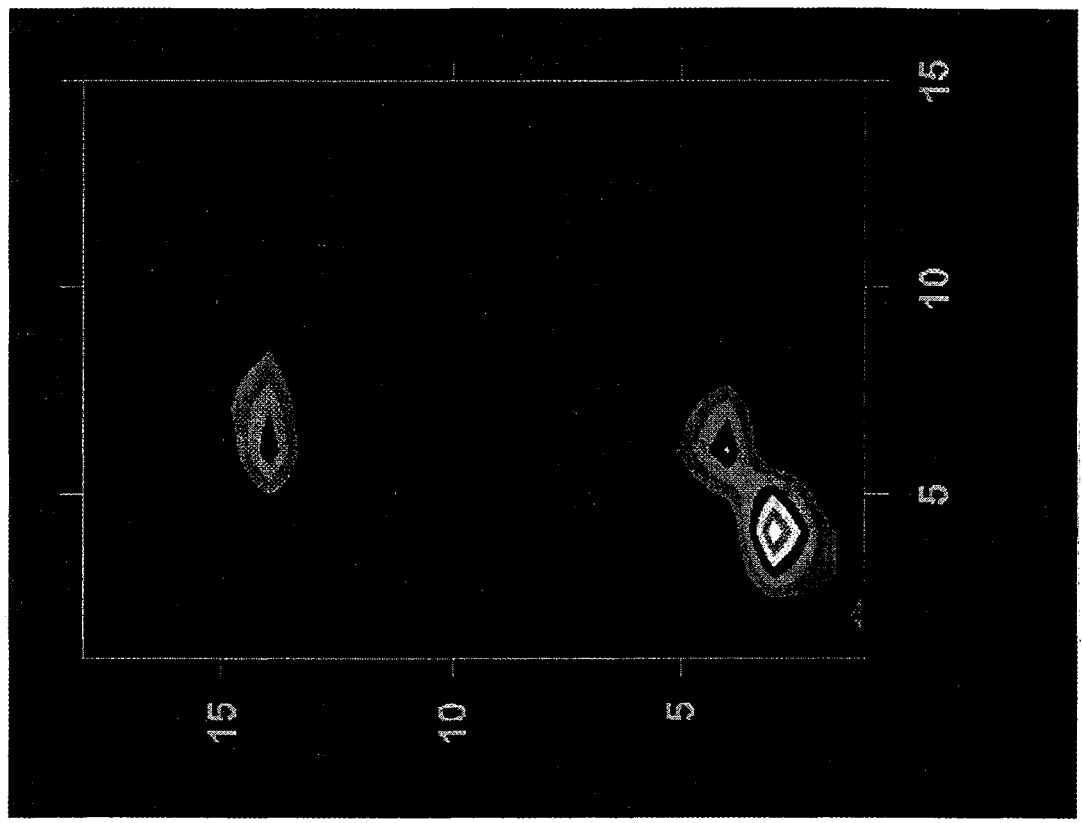
FIGS. 22A-22B show the results of a confocal Raman spectroscopy analysis of the constitution of a product according to the invention.
Figure 22A:

FIG. 22A shows a visual image of the sample, in which the needle-like QS crystals are visible. The two crosses indicate the Raman mapping area, which was 15×18 µm. FIG. 22B is a contour map based on integration of the signal from the band at 1370 cm$^{-1}$ that corresponds to the vibration of quinine. This band is not present in the spectrum of the pure EC polymer; its absence is indicated by the darkest shaded outer regions in FIG. 22B. The white areas represent pure QS.

FIG. 22B shows clearly that the product particles contain outer regions of pure EC and are thus completely "coated". Some also contain a QS "core" from which the EC protectant is completely absent. Other shaded areas in FIG. 22B reflect the intensity scale gradient of the 1370 cm$^{-1}$ spectral band and therefore indicate different drug:polymer ratios. These contours indicate not the existence of different compounds or discrete phases but a gradual change in the QS:EC concentration ratio between the core and the surface of the particle.

Experimental Examples E

These examples investigated the residual solvent content and stability of ethyl cellulose (EC)-coated quinine sulphate (QS) prepared according to embodiments of the invention.

The product of Example A7 (50% w/w QS in EC) was analyzed for residual solvent (ethanol) content using the head space gas chromatography method (Genesis™ Headspace Analyzer fitted on the Varian™ 3400 Series chromatograph).

The analysis showed a residual ethanol content of less than 500 ppm, which represents the lower quantifiable limit. This is also much lower than the limit specified in the ICH (International Conference on Harmonization of Technical Requirements for Registration of Pharmaceuticals for Human Use) guidelines, which is currently 5000 ppm for ethanol.

For the assessment of stability, 200 mg of the Example A6 product (60% w/w QS in EC) was stored for a month at room temperature and 100% relative humidity, alongside a sample of the as-received pure QS. The sample prepared according to embodiments of the invention showed no change in powder physical appearance or flow properties after storage. In contrast the uncoated QS showed signs of partial caking and a lower degree of powder flowability. This indicates that the invented product had an effective polymer coating, adequate to protect the encapsulated active from environmental humidity and enhance its storage stability.

While the foregoing is directed to embodiments of the invention, other and further embodiments of the invention may be devised without departing from the basic scope thereof, and the scope thereof is determined by the claims that follow.

The invention claimed is:

1. A method of preparing a particulate co-formulation having a non-homogeneous distribution of active substance and a polymeric additive using a solution enhanced dispersion by supercritical fluids particle formulation process under mild conditions, the method comprising:
  (i) dissolving an active substance and a polymeric additive in a vehicle to form a single phase target solution, wherein the active substance is less soluble in the vehicle than the additive, and further wherein the amount of additive dissolved in the target solution is an amount effective to form a concentration of additive in the target solution between 1 and 2 percent weight/volume;
  (ii) co-introducing into a particle formation vessel via a fluid inlet nozzle having two or more coaxial, concentric passages, (a) a supercritical fluid that is miscible in all proportions with the vehicle and in which the active substance and the additive are insoluble or substantially insoluble, and (b) the target solution, such that the supercritical fluid and target solution enter the vessel at the same point and under operating conditions effective to disperse the target solution in the supercritical fluid and extract the vehicle therefrom, wherein the operating conditions comprise a temperature that is between 1.01 and 1.05 times the critical temperature, in Kelvin, of the supercritical fluid, a pressure that is between 1.05 and 1.4 times the critical pressure, in bar, of the supercritical fluid, and fluid flow rates of the supercritical fluid and the target solution effective to achieve a vehicle supercritical fluid mole ratio of between 5 and 10% at the point of target solution supercritical fluid contact, to thereby minimize the rate of vehicle extraction by the supercritical fluid, and form a co-precipitated particulate product that is a solid dispersion of the active substance and the additive,
  wherein the particles of the particulate product have a finite gradient in relative additive concentration that increases radially outwards from the core to the surface of the particles, such that the particles comprise a polymer additive-rich surface region but do not possess separate core and coating layers with a distinct physical boundary between them.

2. The method of claim 1, wherein the active substance is selected from the group consisting of pharmaceutically active substances, herbicides, pesticides, foodstuffs, and a nutraceuticals.

3. The method of claim 2, wherein the active substance is a pharmaceutically active substance.

4. The method of claim 1, wherein the active substance is crystalline.

5. The method of claim 1, wherein the additive is a hydrophobic polymer.

6. The method of claim 1, wherein the additive is selected from celluloses, phthalates, acrylates, methacrylates, polyoxyalkylenes and their copolymers, vinyl polymers, homo- and co-polymers of hydroxy acids, and mixtures of the foregoing.

7. The method of claim 1, where the solubility of the active substance and the additive in the vehicle are each in a range of about 0.5-40% w/v.

8. The method of claim 1, where the supercritical fluid is selected from supercritical carbon dioxide, nitrogen, nitrous oxide, sulfur hexafluoride, xenon, ethane, ethylene, chlorotrifluoromethane, chlorodifluoromethane, dichloromethane, trifluoromethane, helium, neon, or a supercritical mixture of any of the foregoing.

9. The method of claim 8, wherein the supercritical fluid is supercritical carbon dioxide.

10. The method of claim 1, wherein the supercritical fluid optionally comprises a co-solvent.

11. The method of claim 1, wherein the relative concentration of the additive in the particles of the particulate product is up to about 60% by weight.

12. The method of claim 1, wherein the surface of the particles of the particulate product is free of active substance.

13. The method of claim 1, wherein the surface of the particles of the particulate product has a concentration of about 5% or less by weight of the active substance.

14. The method of claim 1, wherein the particles of the particulate product are spherical or approximately spherical particles having a volume mean diameter of less than 100 μm, or needle-like particles having a volume mean length within a range from about 5 μm to about 100 μm and a volume mean thickness within a range from about 0.5 μm to about 5 μm, or plate-like particles having a volume mean thickness within a range from about 0.5 μm to about 5 μm.

15. The method of claim 14, wherein the particles of the particulate product are spherical or approximately spherical particles having a volume mean diameter within a range from about 0.5 µm to about 20 µm.

16. The method of claim 15, wherein the particles of the particulate product have a volume mean diameter within a range from about 0.5 µm to about 10 µm.

17. The method of claim 9, wherein the flow rate of the supercritical fluid is about 20 mL/min and the flow rate of the target solution is 1 mL/min or greater.

* * * * *